US011357442B2

(12) United States Patent
Doran et al.

(10) Patent No.: US 11,357,442 B2
(45) Date of Patent: Jun. 14, 2022

(54) COMBINED STIMULATOR AND ELECTRODE ASSEMBLY FOR MOUSE ELECTRORETINOGRAPHY (ERG)

(71) Applicant: Diagnosys LLC, Lowell, MA (US)

(72) Inventors: Bruce Doran, Westford, MA (US); Marc Chabot, Hollis, NH (US)

(73) Assignee: Diagnosys LLC, Lowell, MA (US)

( * ) Notice: Subject to any disclaimer, the term of this patent is extended or adjusted under 35 U.S.C. 154(b) by 433 days.

(21) Appl. No.: 16/167,201

(22) Filed: Oct. 22, 2018

(65) Prior Publication Data

US 2019/0053733 A1 Feb. 21, 2019

Related U.S. Application Data

(63) Continuation-in-part of application No. 15/153,286, filed on May 12, 2016, now Pat. No. 10,820,824.

(60) Provisional application No. 62/575,235, filed on Oct. 20, 2017, provisional application No. 62/160,503, filed on May 12, 2015.

(51) Int. Cl.

| | |
|---|---|
| ***A61B 5/398*** | (2021.01) |
| ***A61B 5/00*** | (2006.01) |
| ***A61B 5/291*** | (2021.01) |

(52) U.S. Cl.

CPC .............. *A61B 5/398* (2021.01); *A61B 5/291* (2021.01); *A61B 5/6821* (2013.01); *A61B 2562/0209* (2013.01)

(58) Field of Classification Search

CPC ... A61B 5/6821; A61B 5/0496; A61B 3/0008; A61B 2090/306; A61B 2503/40; A61B 2503/42; A61B 2562/0209; A61B 2562/182

See application file for complete search history.

(56) References Cited

U.S. PATENT DOCUMENTS

| | | | | |
|---|---|---|---|---|
| 3,001,441 A * | 9/1961 | Herbert .................... | A61B 3/12 351/221 |
| 3,012,472 A | 12/1961 | Feinberg et al. | |

(Continued)

FOREIGN PATENT DOCUMENTS

| | | |
|---|---|---|
| CN | 101019760 | 8/2017 |
| EP | 0225072 | 6/1987 |

(Continued)

OTHER PUBLICATIONS

ColorDome LabCradle: Advanced Animal ERG Testing, Diagnosys, LLC, Aug. 3, 2017.

(Continued)

*Primary Examiner* — Linda C Dvorak
*Assistant Examiner* — Annabeth E Rodriguez
(74) *Attorney, Agent, or Firm* — Pandiscio & Pandiscio

(57) ABSTRACT

Apparatus for evoking and sensing ophthalmic physiological signals in an eye, the apparatus comprising: an elongated light pipe having a longitudinal axis, a distal end and a proximal end, the distal end terminating in a spheroidal recess; and an electrode having a distal end and a proximal end, the electrode being mounted to the elongated light pipe and extending proximally along the elongated light pipe so that the distal end of the electrode terminates at the spheroidal recess at the distal end of the elongated light pipe.

25 Claims, 33 Drawing Sheets

(56) References Cited

U.S. PATENT DOCUMENTS

| | | | | |
|---|---|---|---|---|
| 3,439,157 | A * | 4/1969 | Myles | G02B 6/0001 362/551 |
| 4,131,113 | A * | 12/1978 | Fender | A61B 5/398 600/558 |
| 4,362,164 | A | 12/1982 | Little et al. | |
| 4,618,230 | A | 10/1986 | Ens et al. | |
| 4,740,072 | A | 4/1988 | Griffin et al. | |
| 4,806,289 | A | 2/1989 | Laursen et al. | |
| 4,874,237 | A * | 10/1989 | Cringle | A61B 5/398 221/221 |
| 4,910,090 | A | 3/1990 | Kuhlman et al. | |
| 4,961,423 | A | 10/1990 | Canducci | |
| 5,141,305 | A | 8/1992 | Young | |
| 5,943,116 | A * | 8/1999 | Zeimer | A61B 3/0058 351/221 |
| 6,231,187 | B1 | 5/2001 | Munoz et al. | |
| 8,810,482 | B2 | 8/2014 | Abdollahi et al. | |
| 10,820,824 | B2 * | 11/2020 | Doran | A61B 5/398 |
| 2003/0020875 | A1 * | 1/2003 | Sperling | A61B 5/398 351/206 |
| 2003/0149350 | A1 | 8/2003 | Porciatti | |
| 2005/0245796 | A1 * | 11/2005 | Woods | A61B 5/6821 600/315 |
| 2006/0058857 | A1 | 3/2006 | Tano et al. | |
| 2006/0184062 | A1 | 8/2006 | Greenberg et al. | |
| 2006/0244915 | A1 | 11/2006 | Clemons et al. | |
| 2008/0294066 | A1 | 11/2008 | Hetling et al. | |
| 2010/0091242 | A1 | 4/2010 | Baglini et al. | |
| 2010/0249532 | A1 | 9/2010 | Maddess et al. | |
| 2010/0292999 | A1 | 11/2010 | Verma | |
| 2011/0170064 | A1 | 7/2011 | Taylor | |
| 2012/0069296 | A1 | 3/2012 | Li et al. | |
| 2013/0242077 | A1 | 9/2013 | Lin et al. | |
| 2013/0278899 | A1 | 10/2013 | Waldorf et al. | |
| 2013/0285886 | A1 | 10/2013 | Pombo et al. | |
| 2014/0128763 | A1 | 5/2014 | Fadem | |
| 2014/0333898 | A1 * | 11/2014 | Boate | A61B 3/12 351/221 |
| 2015/0029463 | A1 * | 1/2015 | Hetling | A61B 5/6821 351/219 |
| 2015/0191240 | A1 | 7/2015 | Burchard | |
| 2015/0313467 | A1 | 11/2015 | Sakai et al. | |
| 2017/0014074 | A1 | 1/2017 | Etzkorn et al. | |
| 2017/0042441 | A1 | 2/2017 | Doran et al. | |
| 2017/0127970 | A1 | 5/2017 | Doran et al. | |

FOREIGN PATENT DOCUMENTS

| | | |
|---|---|---|
| EP | 2314201 | 4/2011 |
| WO | WO 2001/078586 | 10/2001 |
| WO | WO 2005/002420 | 1/2005 |
| WO | WO 2008/024222 | 2/2008 |
| WO | WO 2010/066420 | 6/2010 |
| WO | WO 2015/191240 | 12/2015 |
| WO | WO 2016/162796 | 10/2016 |

OTHER PUBLICATIONS

EER Module: Electrically evoked response stimulator, Diagnosys LLC, Jul. 6, 2018.

Electrically Evoked Response: Note, Diagnosys, LLC, Jul. 6, 2018, pp. 1-8.

Frishman, Laura et al., ISCEV extended protocol for the photopic negative response (PhNR) of the full-field electroretinogram, Doc Ophthalmol, vol. 136, No. 3, May 31, 2018, pp. 207-211.

Luo, Xunda et al. Retinal Pathway Origins of the Pattern Electroretinogram (PERG), Investigative Ophthalmology & Visual Science, vol. 52, No. 12, 2011, pp. 8571-8584.

Viswanathan, Suresh et al. The Uniform Field and Pattern ERG in Macaques With Experimental Glaucoma: Removal of Spiking Activity, Investigative Ophthalmology & Visual Science, vol. 41, No. 9, 2000, pp. 2797-2810.

Burr-Brown Products From Texas Instruments, Single-Supply Differential Amplifier, Texas Instruments Incorporated, 2001.

Heath, Janet, Amplifiers: What do rail-to-rail and single supply mean?, Analog IC Tips, 2017, https://www.analogictips.com/amplifiers-rail-to-rail-single-supply-mean/.

Matsumoto, Celso S. et al., Pattern Visual Evoked Potentials Elicited by Organic Electroluminescence Screen, BioMed Research International, vol. 2014, pp. 1-6.

Potts et al., The Electrically Evoked Response of the Visual System (EER), Investigative Ophthamology & Visual Science, vol. 7, No. 3, Jun. 1968, pp. 269-278.

* cited by examiner

Mouse ERG electrode

Support System

COMBINED STIMULATOR AND ELECTRODE ASSEMBLY FOR MOUSE ELECTRORETINOGRAPHY (ERG)

REFERENCE TO PENDING PRIOR PATENT APPLICATIONS

This patent application:

(1) is a continuation-in-part of U.S. patent application Ser. No. 15/153,286, filed May 12, 2016 by Diagnosys LLC and Bruce Doran et al. for COMBINED STIMULATOR AND BIPOLAR ELECTRODE ASSEMBLY FOR MOUSE ELECTRORETINOGRAPHY (ERG), which patent application in turn claims benefit of:

(A) prior U.S. Provisional Patent Application Ser. No. 62/160,503, filed May 12, 2015 by Diagnosys LLC and Bruce Doran et al. for COMBINED STIMULATOR AND BIPOLAR ELECTRODE ASSEMBLY FOR MOUSE ELECTRORETINOGRAPHY (ERG); and (2) claims benefit of prior U.S. Provisional Patent Application Ser. No. 62/575,235, filed Oct. 20, 2017 by Diagnosys LLC and Bruce Doran et al. for COMBINED STIMULATOR AND BIPOLAR ELECTRODE ASSEMBLY FOR MOUSE ELECTRORETINOGRAPHY (ERG).

The three (3) above-identified patent applications are hereby incorporated herein by reference.

FIELD OF THE INVENTION

This invention relates generally to apparatus and methods for the assessment of electrophysiological signals, and more particularly to apparatus and methods for the assessment of ophthalmic electrophysiological signals.

BACKGROUND OF THE INVENTION

Full-field ophthalmic electrophysiology generally involves flashing a light from a large "bowl" into one or both eyes of the test subject, and then measuring the response from the retina of the eye or eyes of the test subject using electrodes, i.e., (an) active electrode(s) which contact(s) the eye(s) of the test subject and other electrodes (reference and ground electrodes) which contact other portions of the test subject. This procedure is sometimes referred to as electroretinography (ERG).

Clinically, the hardest part of performing ophthalmic electrophysiology is properly connecting the electrodes to the test subject and, more particularly, properly connecting the active electrode to the eye of the test subject.

In some cases the ophthalmic electrophysiology must be conducted on humans. In other cases the ophthalmic electrophysiology must be conducted on small rodents of the sort commonly used in laboratory experiments, e.g., mice, rats, guinea pigs, and other small animals (for the purposes of the present invention, such animals will generally be referred to herein as "mice", however, it should be appreciated that such term is meant to be exemplary and not limiting). It will be appreciated that conducting electrophysiology on mice can present issues which may be different from the issues which might arise when conducting electrophysiology on humans.

In present configurations for performing ophthalmic electrophysiology on mice, e.g., with an ERG dome such as that offered by Diagnosys LLC of Lowell, Mass., the anesthetized mouse is placed on a heated platform that maintains its body temperature during the test. At least three electrodes must be attached to the mouse: (i) a ground electrode; (ii) a reference electrode; and (iii) an active (corneal) electrode. In best current practice, the ground and reference electrodes consist of platinum or stainless steel needles, and the active electrode is a silver, silver/silver chloride or platinum wire. One of the needles is used as a ground electrode and is easy to attach to the mouse because its position is not critical—anywhere in the haunch or tail of the mouse will do. Placement of the other two electrodes (i.e., the reference electrode and the active electrode) requires much more care. The remaining needle electrode is the reference electrode. It must be inserted very precisely into the mouse, either at the midline of the scalp, or in the mouth, or in the cheek. Mispositioning of the reference electrode will cause imbalances in the readings between the two eyes of the mouse. The last electrode, the wire electrode, is the active (corneal) electrode. It too must be placed in just the right position on the cornea of the eye in order to avoid biasing the recording: too close to the center of the eye and the wire will block light, too far to the periphery of the eye and the wire will record lower voltages than if placed nearer to the center of the eye. If both eyes of the animal are to be tested, a second corneal wire (i.e., a second active electrode) must be placed on the cornea of the second eye in a position homologous to the position of the first corneal wire (i.e., in a position homologous to the first active electrode). An added complication is that, usually, all this must be done in a room only dimly illuminated by deep red light.

After the three electrodes have been placed on the mouse, the ERG dome is either moved into position over the mouse or the platform supporting the mouse is moved into the dome. Either movement may disturb the electrodes placed on the mouse, which would then require that the electrodes be repositioned. And inasmuch as the mouse is hidden by the dome, if the mouse should wake up (as it sometimes does), the mouse could escape under cover of darkness.

FIG. 1 shows the current Diagnosys mouse ERG dome platform in its open position.

FIG. 2 shows the same Diagnosys mouse ERG dome platform in its closed position.

It will be appreciated that conducting ophthalmic electrophysiology on a mouse is time-consuming and requires personnel with specialized skills. For this reason, ophthalmic electrophysiology is sometimes not performed on mice even where the results of performing ophthalmic electrophysiology could be beneficial. By way of example but not limitation, the National Institutes of Health (NIH) has an impending campaign to phenotype more than 300,000 mutated mice. Among other things, the mice are being tested for deficits analogous to human eye disease. Although some of these deficits can only be detected using ophthalmic electrophysiology, electrophysiology was initially excluded from the testing protocols because existing techniques for performing ophthalmic electrophysiology on mice are too time-consuming and require personnel with specialized skills.

Ophthalmic electrophysiology would be significantly easier to perform on mice if there were a way to rapidly and automatically position the active and reference electrodes on the mouse.

There is an existing device (a "contact lens bipolar corneal electrode") that does this effectively for humans, but in its present state the contact lens bipolar corneal electrode is not practical for widespread use with mice.

More particularly, a contact lens bipolar corneal electrode consists of a lid-retracting speculum having a reference electrode embedded in its outer circumference. A contact lens, ringed by the active (corneal) electrode, is suspended by a spring from the inner part of the lid-retracting speculum. Since the active and reference electrodes are both built into the device, the two electrodes occupy the same position on every eye (which is easily adjusted during manufacture to be at the correct position on the eye of the test subject). As a result, the contact lens bipolar corneal electrode provides highly reliable positioning of the active and reference electrodes on the eye of the test subject, and hence provides highly reliable results. A further advantage of the contact lens bipolar corneal electrode is that both electrodes (i.e., the active electrode and the reference electrode) touch the tear film of the eye, making excellent electrical contact with the test subject without special preparation.

FIG. 3 shows a human contact lens bipolar corneal electrode which was introduced by Diagnosys in 1986.

FIG. 4 shows another human contact lens bipolar corneal electrode sold by Hansen Ophthalmic Development Laboratories of Coralville, Iowa (sometimes referred to as "Hansen Labs").

As noted above, human contact lens bipolar corneal electrodes work effectively, but mouse contact lens bipolar corneal electrodes are impractical for widespread use with mice. More particularly, a mouse contact lens bipolar corneal electrode is available from Hansen Ophthalmic Development Laboratories, but the mouse contact lens bipolar corneal electrode is impractically delicate, expensive, and hard to make. The basic problem with the mouse contact lens bipolar corneal electrode sold by Hansen Ophthalmic Development Laboratories is that the manufacturer does not know how its customers are going to use the device (a customer may have an application that needs the animal to view an image) and so the manufacturer has to start by wrapping the active (corneal) electrode around an optically "good", zero-power mouse contact lens, and this is a challenging task.

Another problem with mouse contact lens bipolar corneal electrodes is that, if anything, they slow the testing process down rather than speed it up. More particularly, the mouse contact lens bipolar corneal electrodes are so delicate and sensitive that they require great care and skill in order to place them properly on the eye of the mouse. By way of example but not limitation, it is very easy to accidentally cover the mouse contact lens bipolar corneal electrodes with saline solution which shorts them out, and they often break during handling. In any case, mouse contact lens bipolar corneal electrodes are so hard to make that they are generally now offered in only monopolar versions, which means that the problem of placing the reference electrode on the mouse is still left to the user. The only real advantage of current mouse contact lens bipolar corneal electrodes over current wire electrodes is that the mouse contact lens bipolar corneal electrodes cover the cornea and prevent the formation of cataracts in the mouse due to drying.

FIG. 5 shows the mouse contact lens bipolar corneal electrode sold by Hansen Ophthalmic Development Laboratories.

Thus there is a need for a new and improved approach for quickly and easily performing ophthalmic electrophysiology on mice.

SUMMARY OF THE INVENTION

The present invention comprises the provision and use of a new and improved method and apparatus for quickly and easily performing ophthalmic electrophysiology on mice.

In one form of the present invention, there is provided apparatus for evoking and sensing ophthalmic physiological signals in an eye, the apparatus comprising:

an elongated light pipe having a longitudinal axis, a distal end and a proximal end, the distal end terminating in a spheroidal recess;

an active electrode having a distal end and a proximal end, the active electrode being mounted to the elongated light pipe and extending proximally along the elongated light pipe so that the distal end of the active electrode terminates at the spheroidal recess at the distal end of the elongated light pipe; and a reference electrode having a distal end and a proximal end, the reference electrode being mounted to the elongated light pipe and extending proximally along the elongated light pipe so that the distal end of the reference electrode terminates at the spheroidal recess at the distal end of the elongated light pipe;

wherein the distal end of the active electrode is located closer to the longitudinal axis of the elongated light pipe than the distal end of the reference electrode.

In another form of the present invention, there is provided a method for evoking and sensing ophthalmic physiological signals in an eye, the method comprising:

providing apparatus comprising:

- an elongated light pipe having a longitudinal axis, a distal end and a proximal end, the distal end terminating in a spheroidal recess;
- an active electrode having a distal end and a proximal end, the active electrode being mounted to the elongated light pipe and extending proximally along the elongated light pipe so that the distal end of the active electrode terminates at the spheroidal recess at the distal end of the elongated light pipe; and
- a reference electrode having a distal end and a proximal end, the reference electrode being mounted to the elongated light pipe and extending proximally along the elongated light pipe so that the distal end of the reference electrode terminates at the spheroidal recess at the distal end of the elongated light pipe;
- wherein the distal end of the active electrode is located closer to the longitudinal axis of the elongated light pipe than the distal end of the reference electrode;

positioning the elongated light pipe against an eye of a test subject; and introducing light into the proximal end of the elongated light pipe.

Preferably the apparatus further comprises a light source, whereby to form a combined stimulator and bipolar electrode assembly.

In another form of the present invention, the active electrode may terminate in a circular ring at the distal end of the elongated light pipe, and the reference electrode may be omitted, whereby to form a combined stimulator and monopolar electrode assembly.

And in another form of the present invention, the light source may comprise a pattern stimulator, and the elongated light pipe may be replaced by a tapered (e.g., conical or frustoconical) light pipe, whereby to form a combined pattern stimulator and monopolar electrode assembly.

And in another preferred form of the invention, there is provided apparatus for evoking and sensing ophthalmic physiological signals in an eye, the apparatus comprising:

an elongated light pipe having a longitudinal axis, a distal end and a proximal end, the distal end terminating in a spheroidal recess; and an electrode having a distal end and a proximal end, the electrode being mounted to the elongated light pipe and extending proximally along the elongated light pipe so that the distal end of the electrode terminates adjacent to the spheroidal recess at the distal end of the elongated light pipe.

And in another preferred form of the invention, there is provided a method for evoking and sensing ophthalmic physiological signals in an eye, the method comprising:

providing apparatus comprising:

an elongated light pipe having a longitudinal axis, a distal end and a proximal end, the distal end terminating in a spheroidal recess; and an electrode having a distal end and a proximal end, the electrode being mounted to the elongated light pipe and extending proximally along the elongated light pipe so that the distal end of the electrode terminates at the spheroidal recess at the distal end of the elongated light pipe;

positioning the elongated light pipe against an eye of a test subject; and introducing light into the proximal end of the elongated light pipe.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
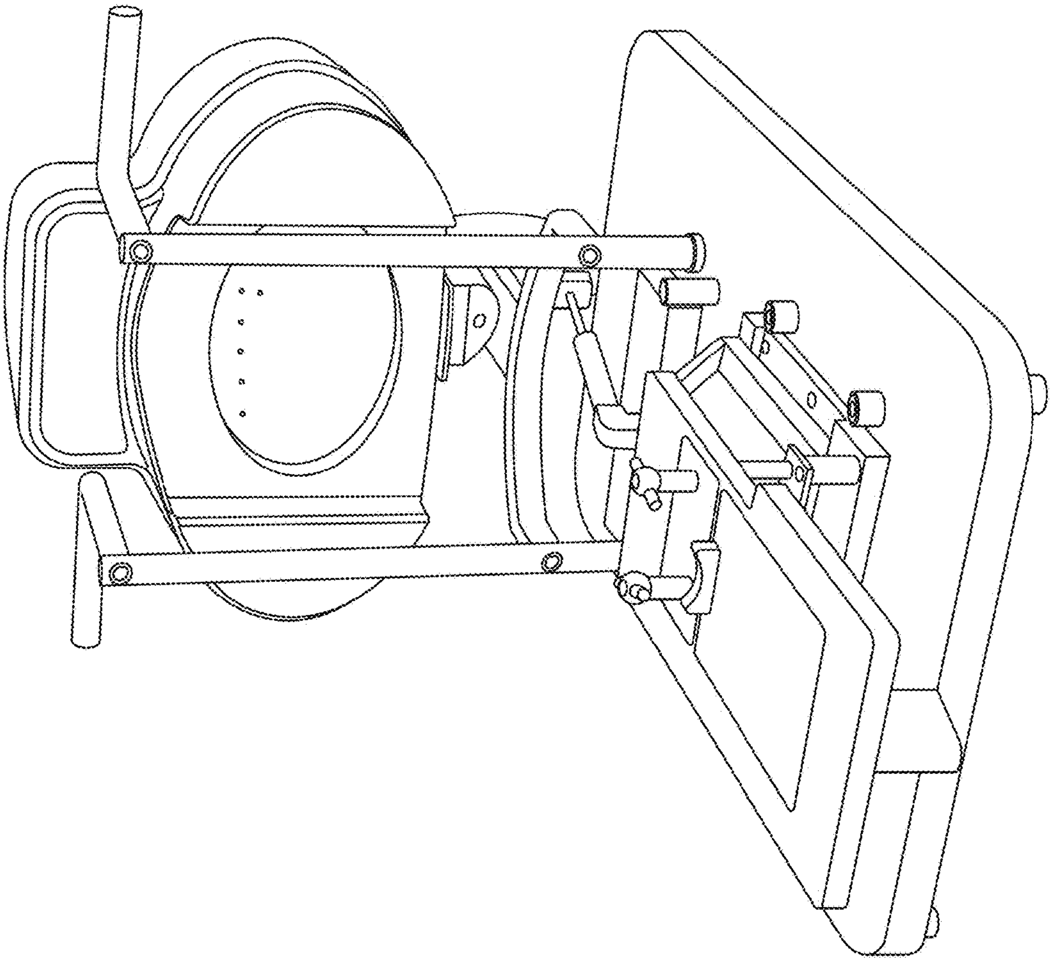
FIGS. 1 and 2 are schematic views showing a prior art mouse ERG dome platform sold by Diagnosys LLC.
Figure 2:
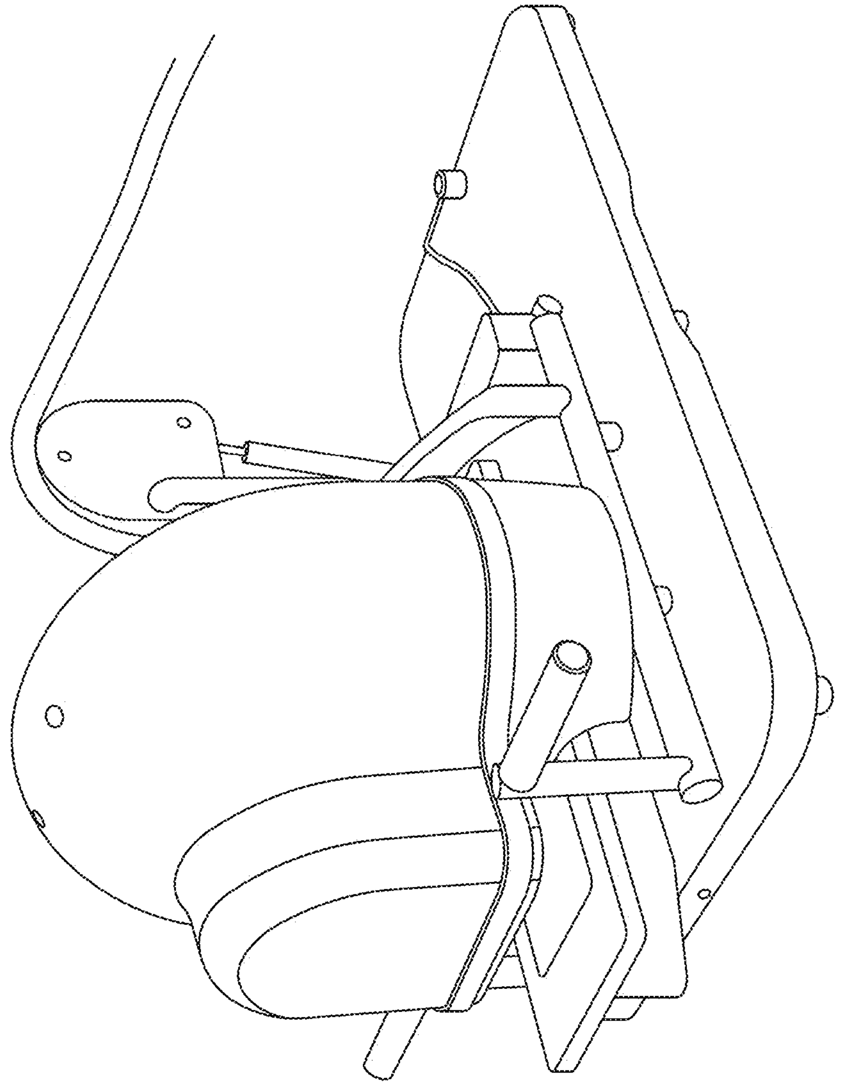
Figure 3:
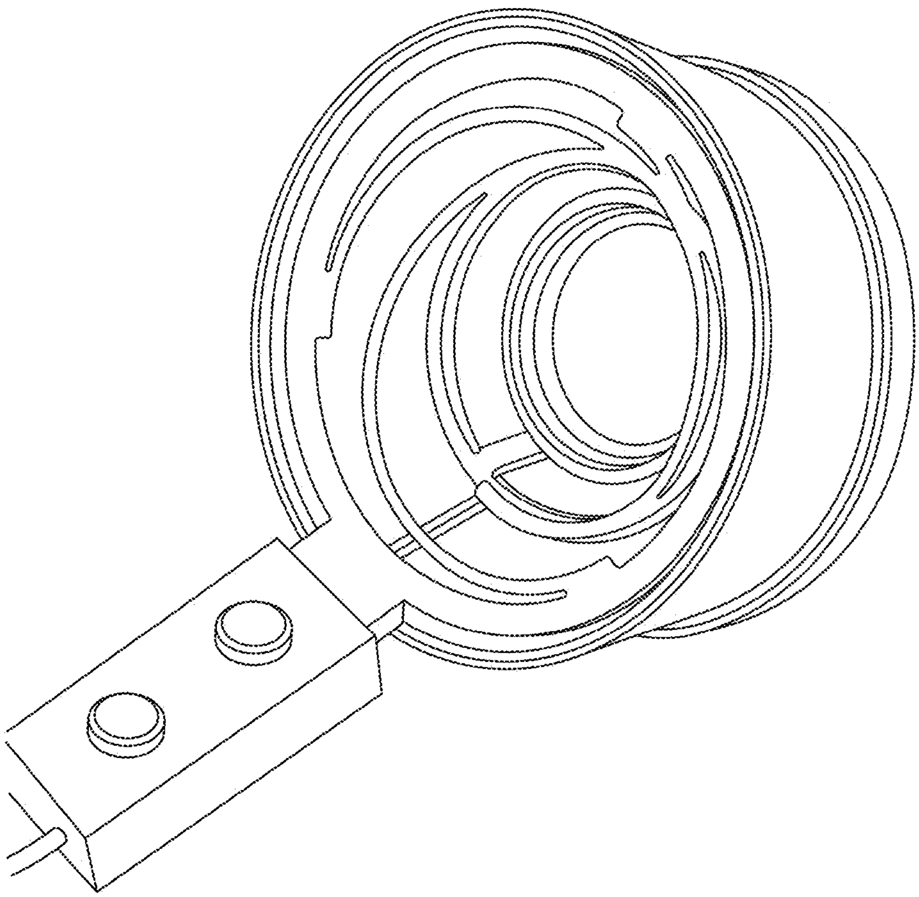
FIG. 3 is a schematic view showing a prior art human contact lens bipolar corneal electrode sold by Diagnosys LLC.
Figure 4:
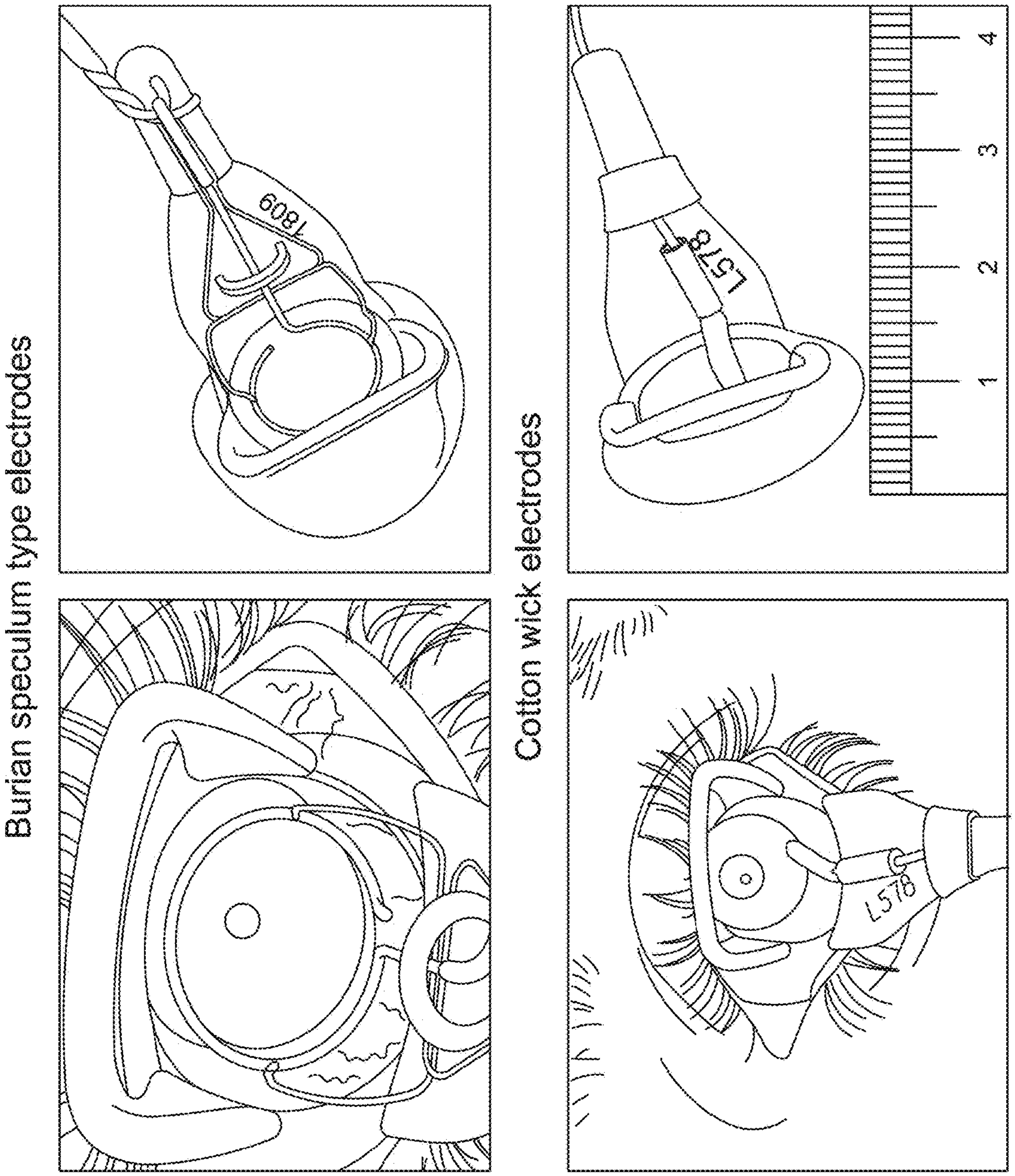
FIG. 4 is a series of schematic views showing prior art human contact lens bipolar corneal electrodes sold by Hansen Ophthalmic Development Laboratories.
Figure 5:
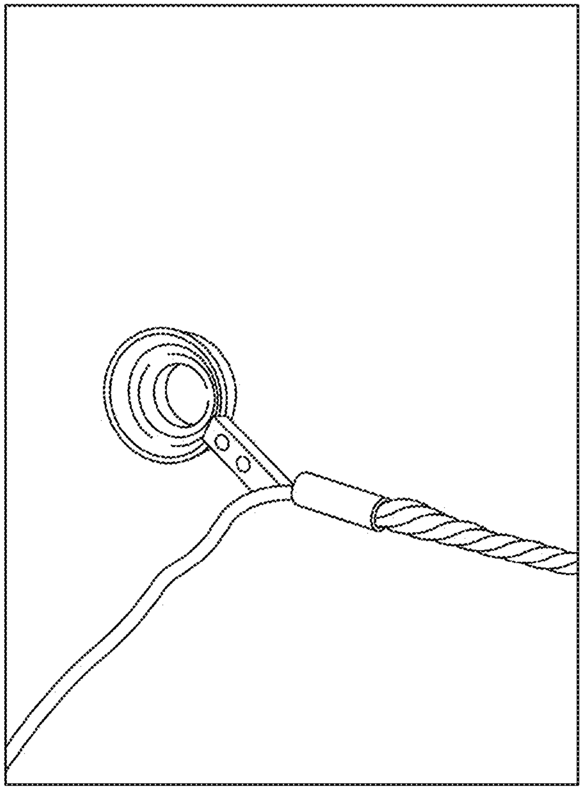
FIG. 5 is a schematic view showing a prior art mouse contact lens bipolar corneal electrode sold by Hansen Ophthalmic Development Laboratories.
Figure 6:
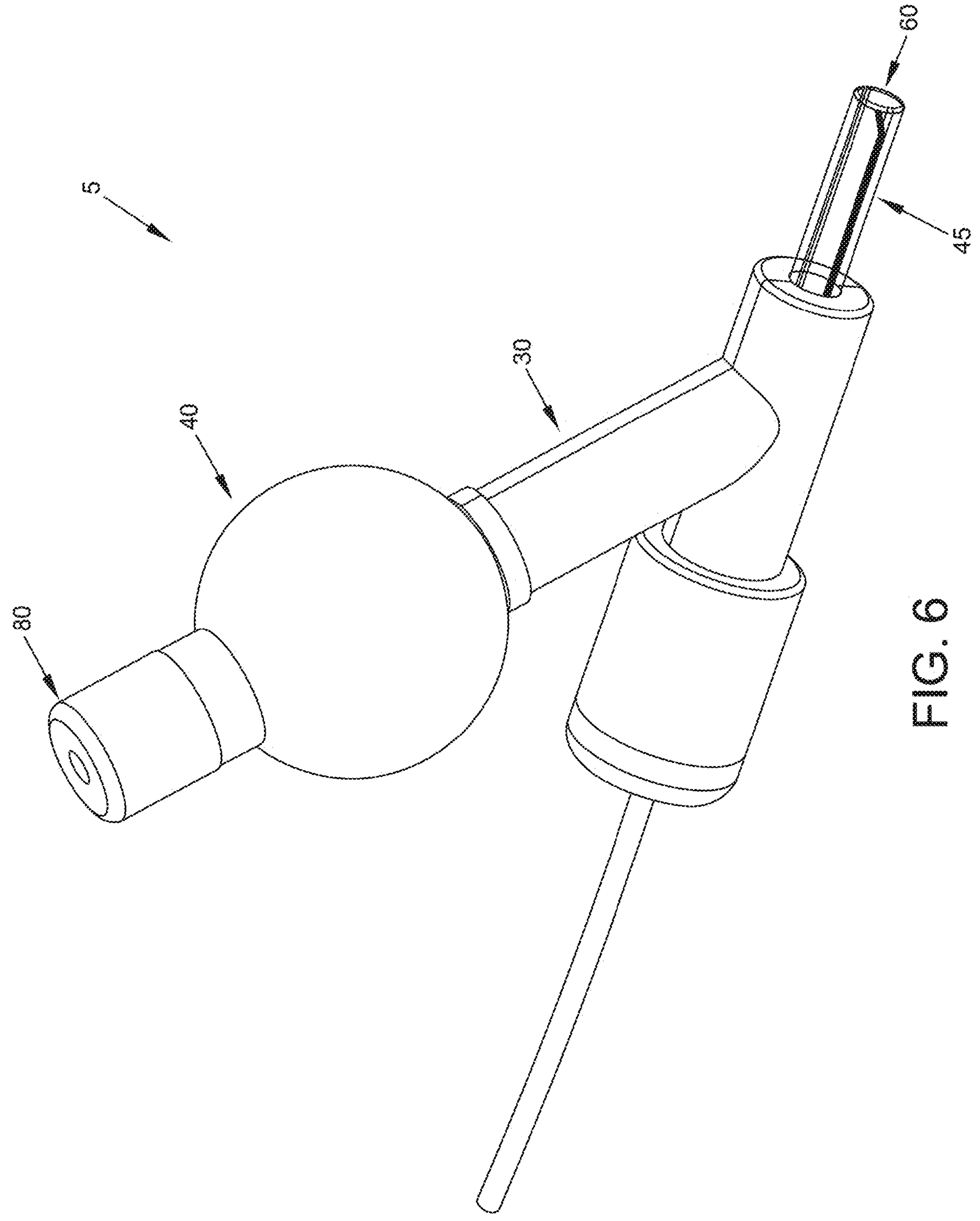
FIGS. 6-12 are schematic views showing novel apparatus for evoking and sensing ophthalmic physiological signals in an eye.
Figure 7:
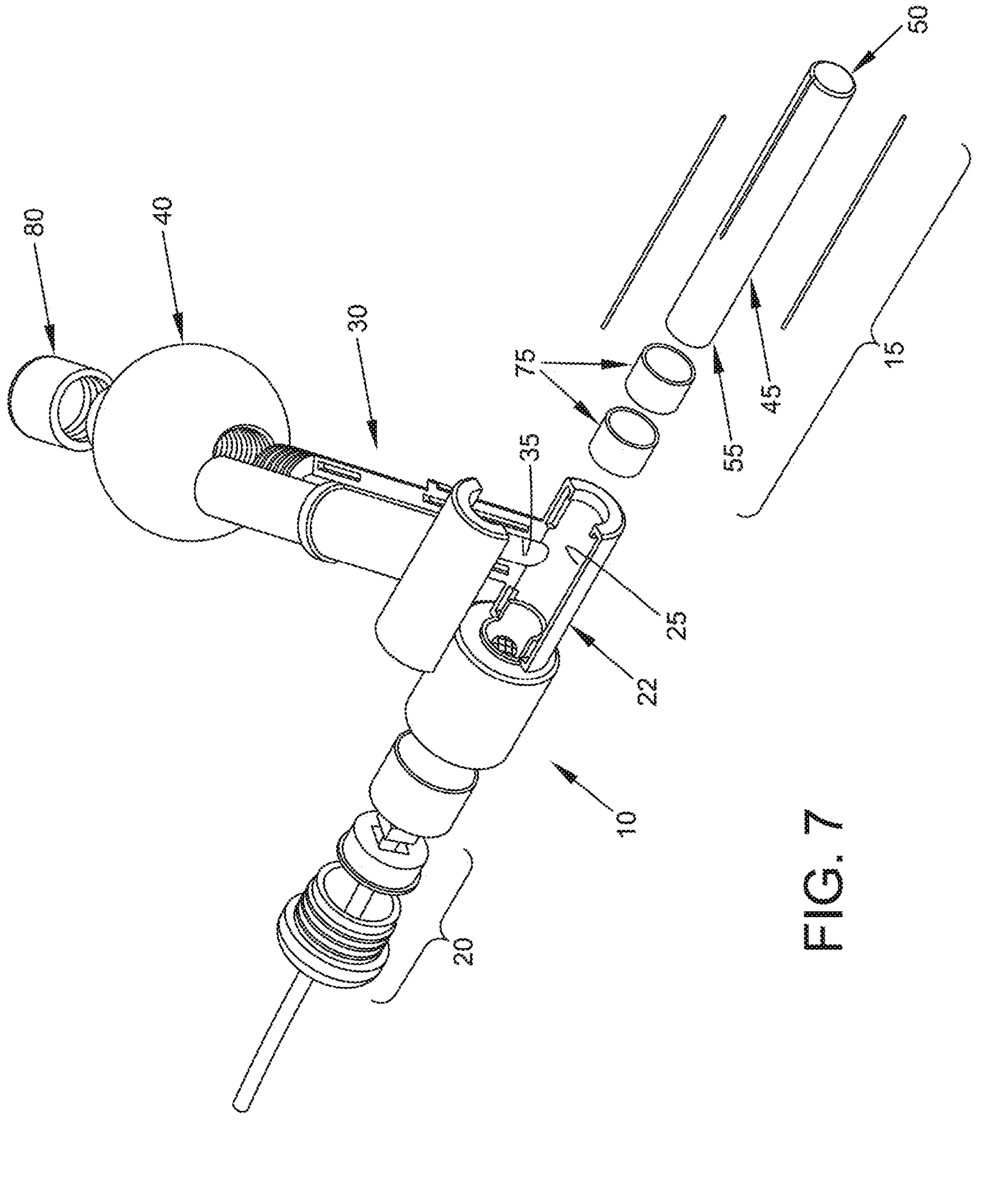
Figure 8:
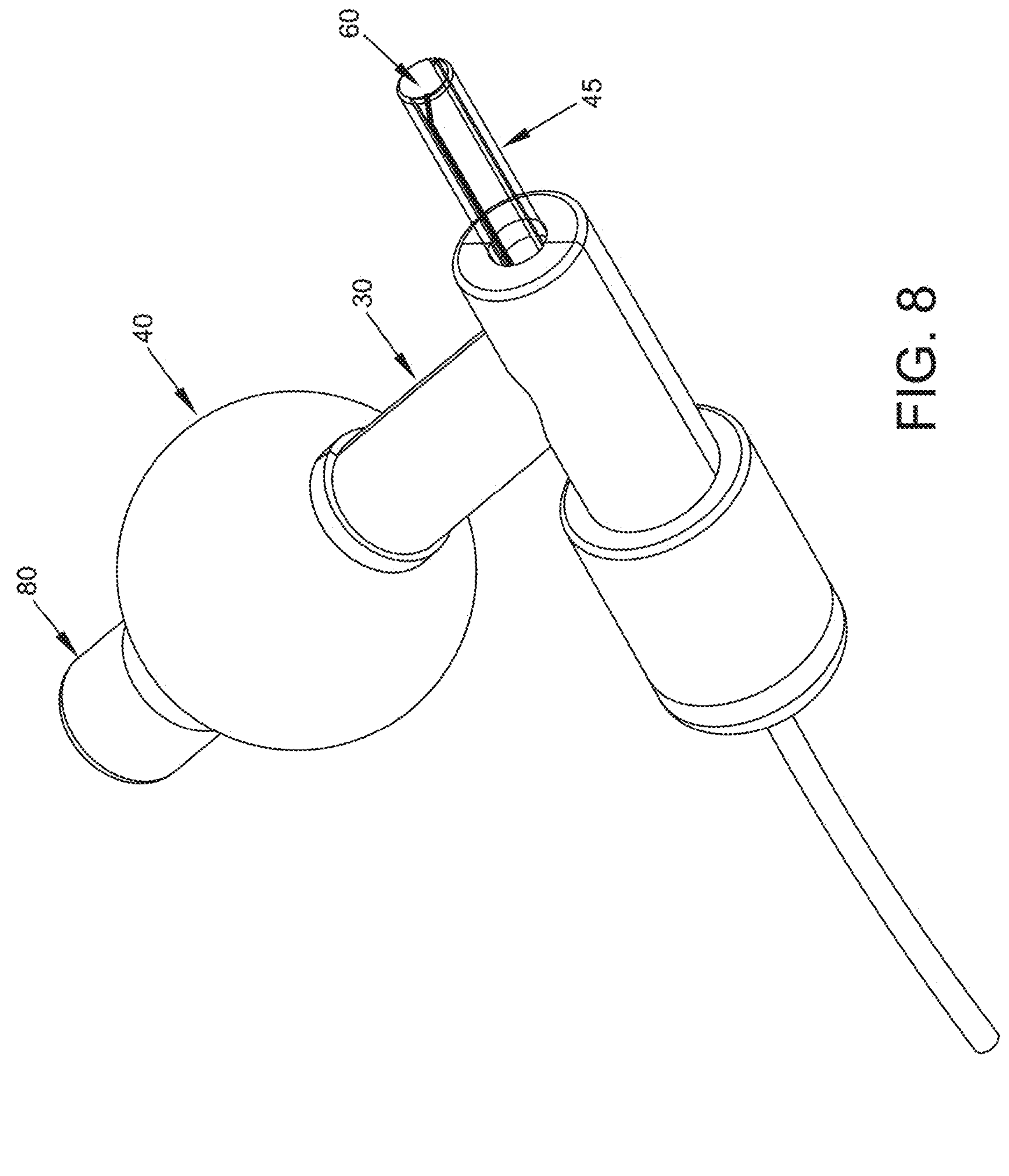
Figure 9:
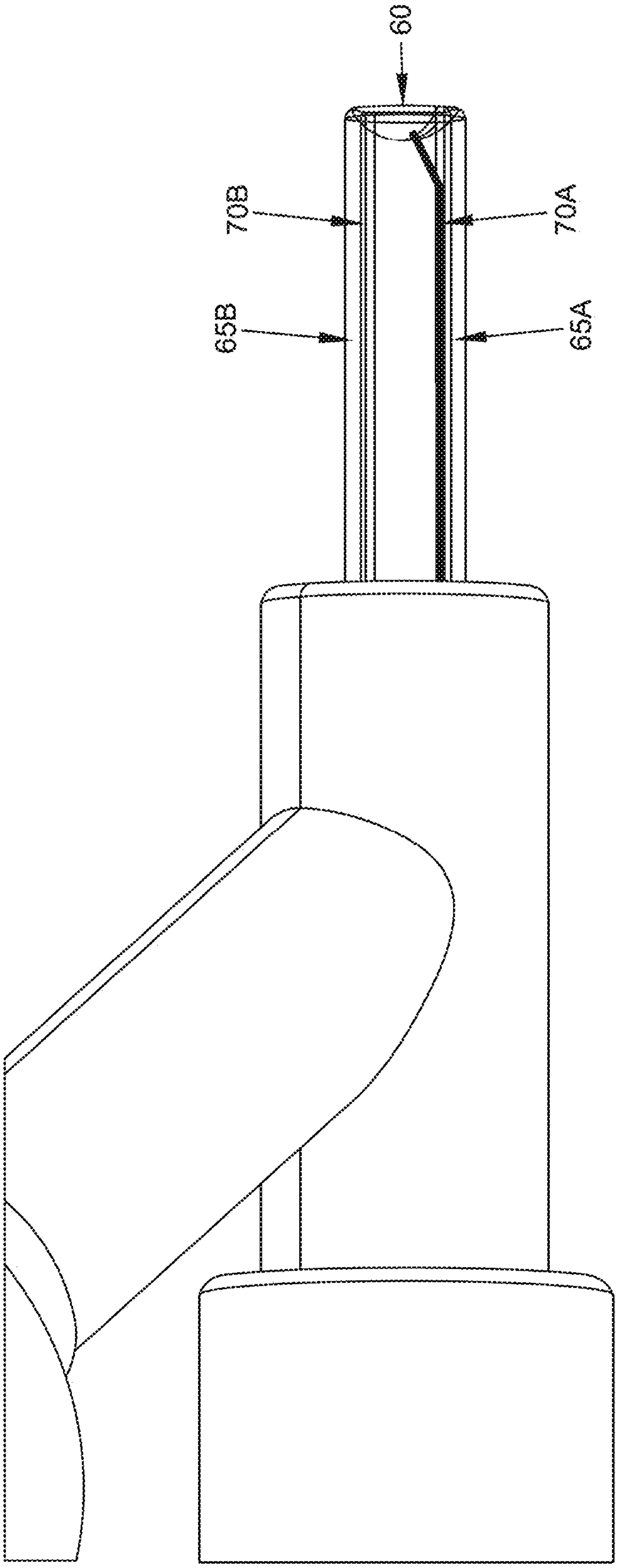
Figure 10:
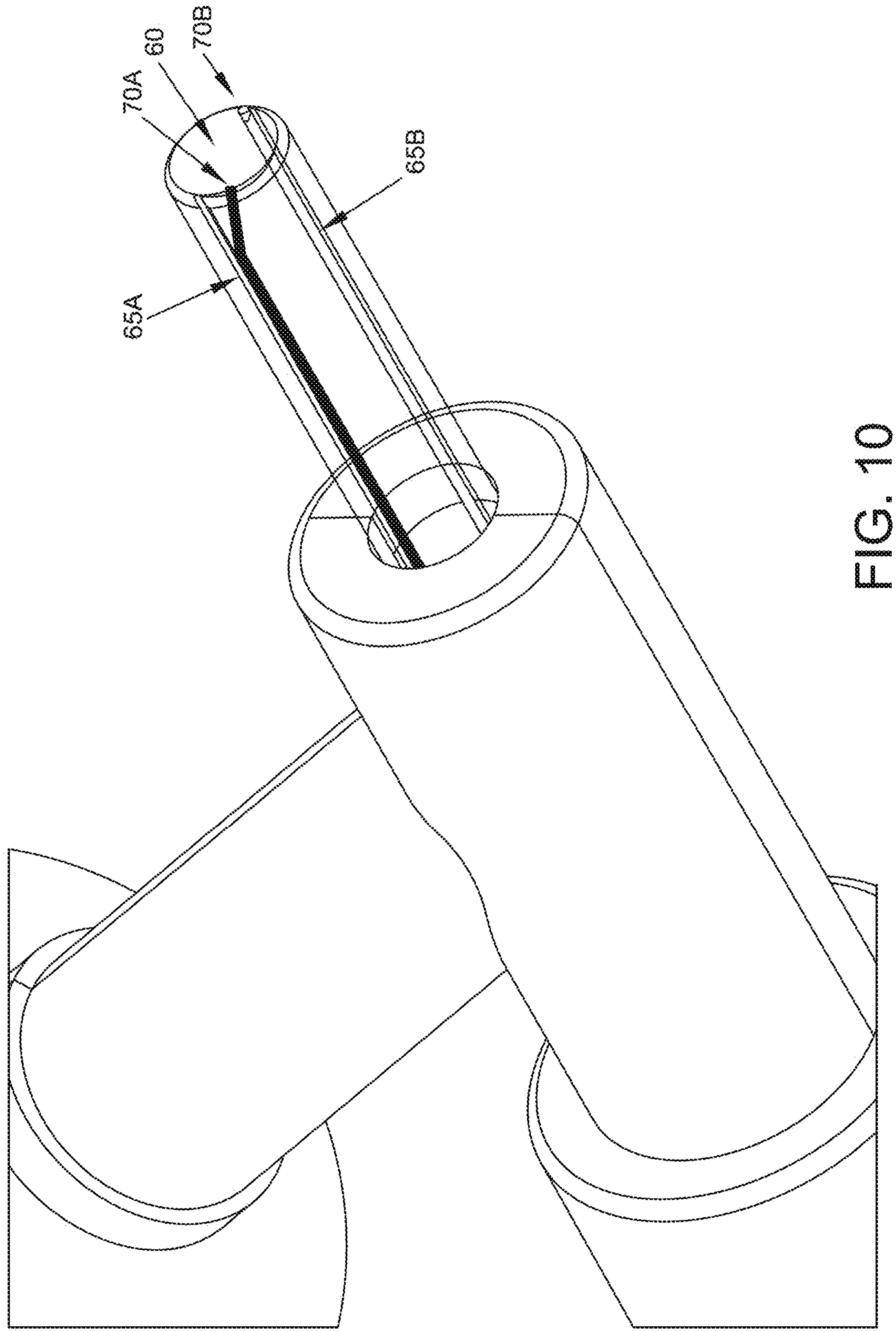
Figure 11:
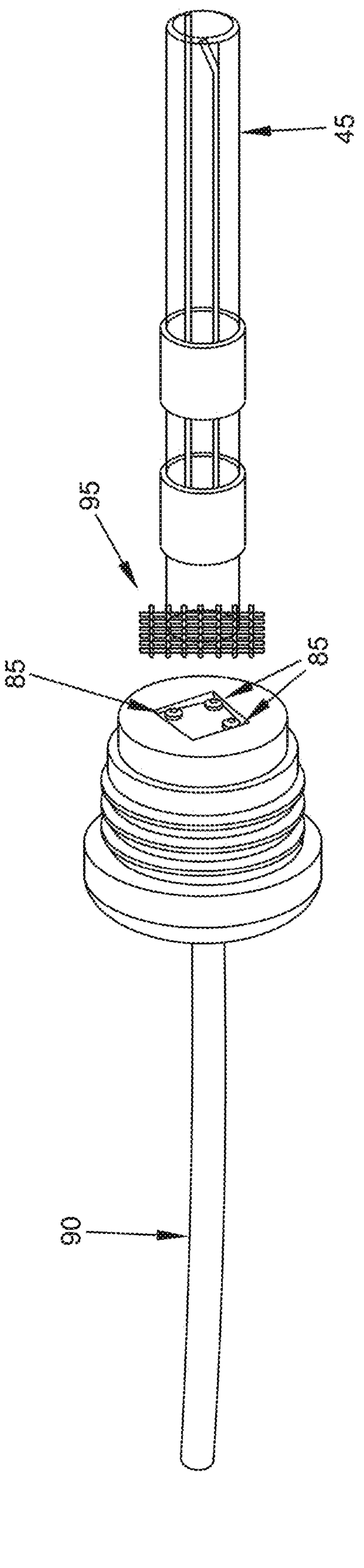

The present invention provides a new and improved approach for quickly and easily performing ophthalmic electrophysiology on mice.

Combined Stimulator and Bipolar Electrode Assembly

In one form of the invention, and looking now at FIGS. 6-11, there is provided a combined stimulator and bipolar electrode assembly 5. Combined stimulator and bipolar electrode assembly 5 generally comprises a housing 10, a light pipe subassembly 15 and a light source subassembly 20.

Housing 10 preferably comprises a main body 22 having a cavity 25 formed therein, and a side arm 30 extending at an angle (e.g., 125 degrees) to the longitudinal axis of main body 22. Side arm 30 includes a cavity 35 formed therein, and a magnetic mount 40 (preferably in the form of a nickel-plated steel ball) secured to side arm 30.

Light pipe subassembly 15 is disposed partially within, and protrudes from, cavity 25 of main body 22. Light pipe subassembly 15 generally comprises a light pipe 45 formed out of a light-transmissive material (e.g., Plexiglas or other acrylic, Lexan or other polycarbonate, or glass, etc.) and having a distal end 50 and a proximal end 55. Light pipe 45 has an elongated configuration, and may be cylindrical (e.g., substantially straight with a substantially circular cross-section), or non-linear pseudo-cylindrical (e.g., bent or curved with a substantially circular cross-section), or light pipe 45 may have another appropriate configuration. Distal end 50 of light pipe 45 has a spheroidal recess 60 formed therein. The radius of curvature of spheroidal recess 60 is preferably similar to the radius of curvature of the eye of a mouse, so that distal end 50 of light pipe 45 can be seated against the outside surface of the eye of a mouse.

Light pipe 45 also comprises a pair of slots 65A, 65B formed in the outer surface of light pipe 45. In one preferred form of the invention, slots 65A, 65B are diametrically opposed to one another. The distal end of slot 65A has a greater depth than the remainder of slot 65A, so that the distal end of slot 65A approaches (but preferably does not reach) the center of spheroidal recess 60.

A platinum (or silver or gold, etc.) wire 70A, which serves as the active electrode for combined stimulator and bipolar electrode assembly 5, is disposed in slot 65A. Note that the distal end of platinum wire 70A follows the floor of slot 65A so that the distal end of platinum wire 70A approaches the center of spheroidal recess 60. The distal end of platinum wire 70A communicates with spheroidal recess 60. Preferably at least the distal portion of slot 65A outboard of wire 70A is filled with an appropriate material (e.g., a light-transmissive, non-conductive, waterproof material) so as to eliminate air gaps between light pipe 45 and the eye of the mouse.

A platinum (or silver or gold, etc.) wire 70B, which serves as the reference electrode for combined stimulator and bipolar electrode assembly 5, is disposed in slot 65B. The distal end of platinum wire 70B also communicates with spheroidal recess 60. Preferably at least the distal portion of slot 65B outboard of wire 70B is filled with an appropriate material (e.g., a light-transmissive, non-conductive, waterproof material) so as to eliminate air gaps between light pipe 45 and the eye of the mouse.

Significantly, the distance between the distal end of platinum wire 70A (which will act as the active electrode) and the distal end of platinum wire 70B (which will act as the reference electrode) is substantially equal to the distance between a portion of the eye which exhibits an evoked physiological signal and a portion of the eye which exhibits a lesser evoked physiological signal (or, preferably, does not exhibit an evoked physiological signal), e.g., the distance between the cornea and the perimeter of the eye.

The intermediate portions of platinum wires 70A, 70B may be held to the body of light pipe 45 with shrink bands 75. The proximal end 55 of light pipe 45 is disposed in cavity 25 of main body 20, and the proximal ends of platinum wires 70A, 70B are passed through cavity 35 of side arm 30 so that they can be brought out the proximal end 80 of side arm 30 for connection to appropriate amplification (e.g., by a differential amplifier) and processing electronics (not shown) for ERG signal processing.

Light source subassembly 20 is disposed within cavity 25 of main body 20. Light source subassembly 20 generally comprises light-emitting diodes (LEDs) 85 for generating light, and any appropriate optics (not shown) required to transmit the light generated by LEDs 85 into the proximal end 55 of light pipe 45, whereupon the light will travel down the length of light pipe 45 to the distal end 50 of light pipe 45. A power line 90 provides power to LEDs 85. Preferably a wire mesh 95 (or similar element) is provided distal to LEDs 85 and proximal to platinum wires 70A, 70B so as to provide electromagnetic interference (EMI) shielding between LEDs 85 and platinum wires 70A, 70B. Alternatively, if desired, other electromagnetic interference (EMI) shielding of the sort well known in the art may be provided between LEDS 85 and platinum wires 70A, 70B.

It will be appreciated that, on account of the foregoing construction, combined stimulator and bipolar electrode assembly 5 can be supported via its magnetic mount 40 for use with an ERG mouse platform, with the proximal ends of platinum wires 70A, 70B being connected to appropriate amplification and processing electronics for ERG signal processing, and with power line 90 being connected to an appropriate source of power.

When a mouse is to be tested, the mouse is placed on an appropriate platform, a ground electrode (not shown) is attached to the mouse (e.g., in the haunch or tail of the animal), and then housing 10 can be moved so as to bring the distal end 50 of light pipe 45 into contact with the eye of the mouse. This action will position the distal end of platinum wire 70A (i.e., the active electrode) at the appropriate position on the eye of the mouse, and will simultaneously position the distal end of platinum wire 70B (i.e., the reference electrode) at another appropriate position on the eye of the mouse (i.e., so that the distal end of platinum wire 70A contacts a portion of the eye which exhibits an evoked physiological signal and the distal end of platinum wire 70B contacts a portion of the eye which exhibits a lesser evoked physiological signal or, preferably, which does not exhibit an evoked physiological signal). When LEDs 85 are thereafter energized, the light from LEDs 85 passes down light pipe 45 and into the eye of the mouse, whereby to stimulate the eye of the mouse. Platinum wires 70A (i.e., the active electrode) and 70B (i.e., the reference electrode) pick up the electrophysiological response of the eye of the mouse as electrical signals, and these electrical signals are passed along platinum wires 70A, 70B to appropriate amplification and processing electronics for ERG signal processing.

Thus it will be seen that with the combined stimulator and bipolar electrode assembly 5 of the present invention, the assembly simultaneously provides (i) the stimulator needed for conducting ophthalmic electrophysiology on a mouse (i.e., LEDs 85 and light pipe 45), (ii) the bipolar electrode (i.e., an active electrode and a reference electrode) needed for conducting ophthalmic electrophysiology on a mouse (i.e., platinum wires 70A, 70B supported by light pipe 45), and (iii) the support structure (e.g., magnetic mount 40) for holding the bipolar electrode securely against the eye of the mouse during testing.

Significantly, mounting platinum wires 70A, 70B to the light pipe 45 provides a robust mechanical support for the platinum wires, making it possible to quickly, easily and precisely position the active electrode (i.e., platinum wire 70A) and the reference electrode (i.e., platinum wire 70B) on the eye of the mouse. At the same time, the small acceptance angle of light pipe 45 restricts the light reaching the eye of the mouse which is being tested to only that light which is being generated by LEDs 85, which eliminates the normal need for a large Ganzfeld to conduct ophthalmic electrophysiology.

Note that LEDs 85 may be a three-color red-green-blue (RGB) system, in which case appropriate electronic drivers are preferably provided to drive RGB LEDs 85 accurately enough to form precisely-defined metameric colors. Alternatively, LEDs 85 may produce ultraviolet (UV) light, which can be desirable in mice.

Light Diffuser, Enlarged Reference Electrode and Red Light Illumination

Figure 12:
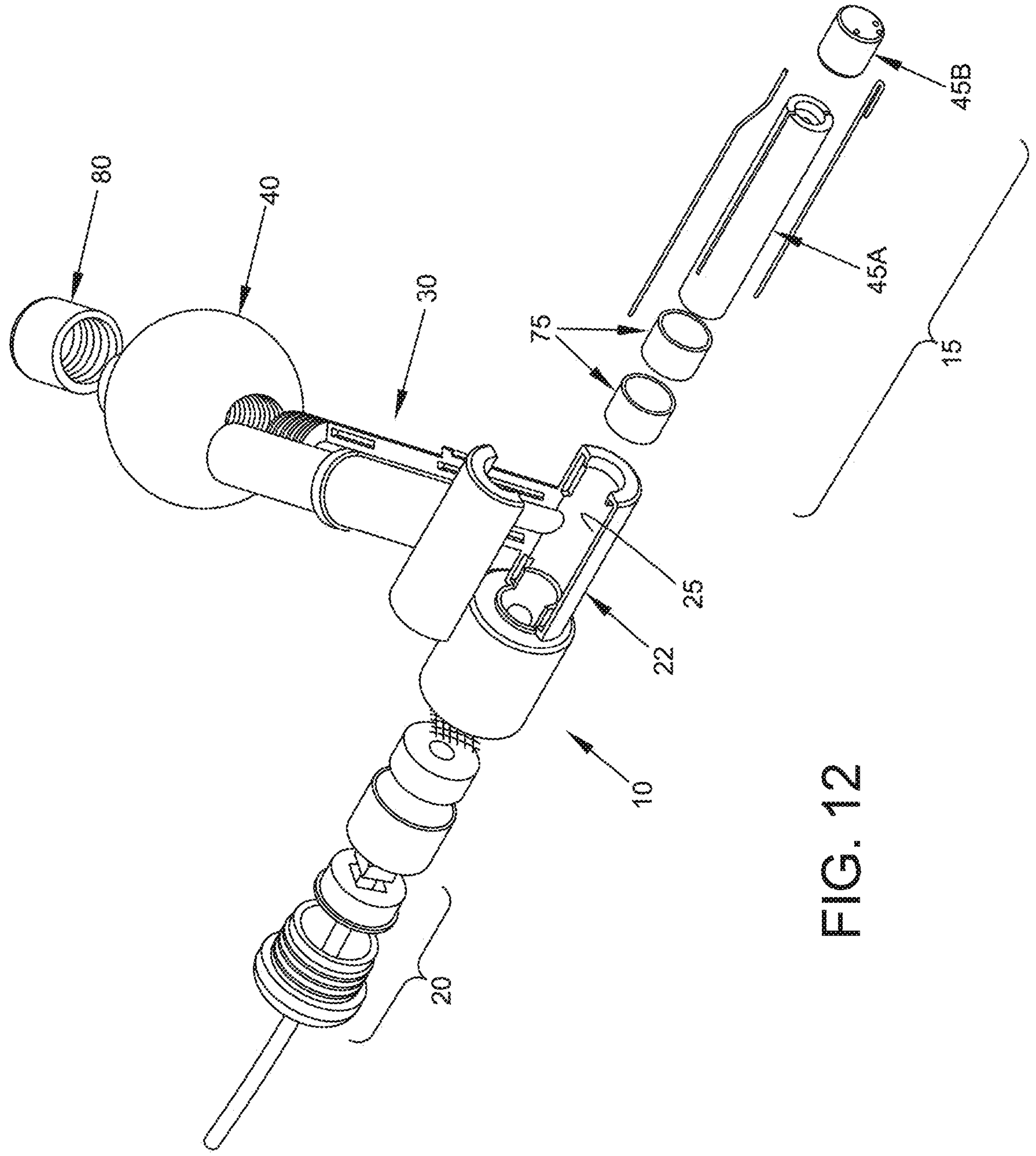

If desired, and looking now at FIG. 12, light pipe 45 may comprise a main body 45A and an end diffuser 45B. End diffuser 45B can, advantageously, help provide full retinal illumination. More particularly, end diffuser 45B acts to broaden the angle at which light exits main body 45A of light pipe 45 and enters the eye of the mouse, and ensures that light exiting the light pipe is distributed equally to all parts of the retina of the mouse. The diffusing material of end diffuser 45B is preferably of non-uniform thickness, i.e., it is made thinner at the edges to compensate for the lower flux density occurring at the perimeter of the light pipe.

Figure 13:
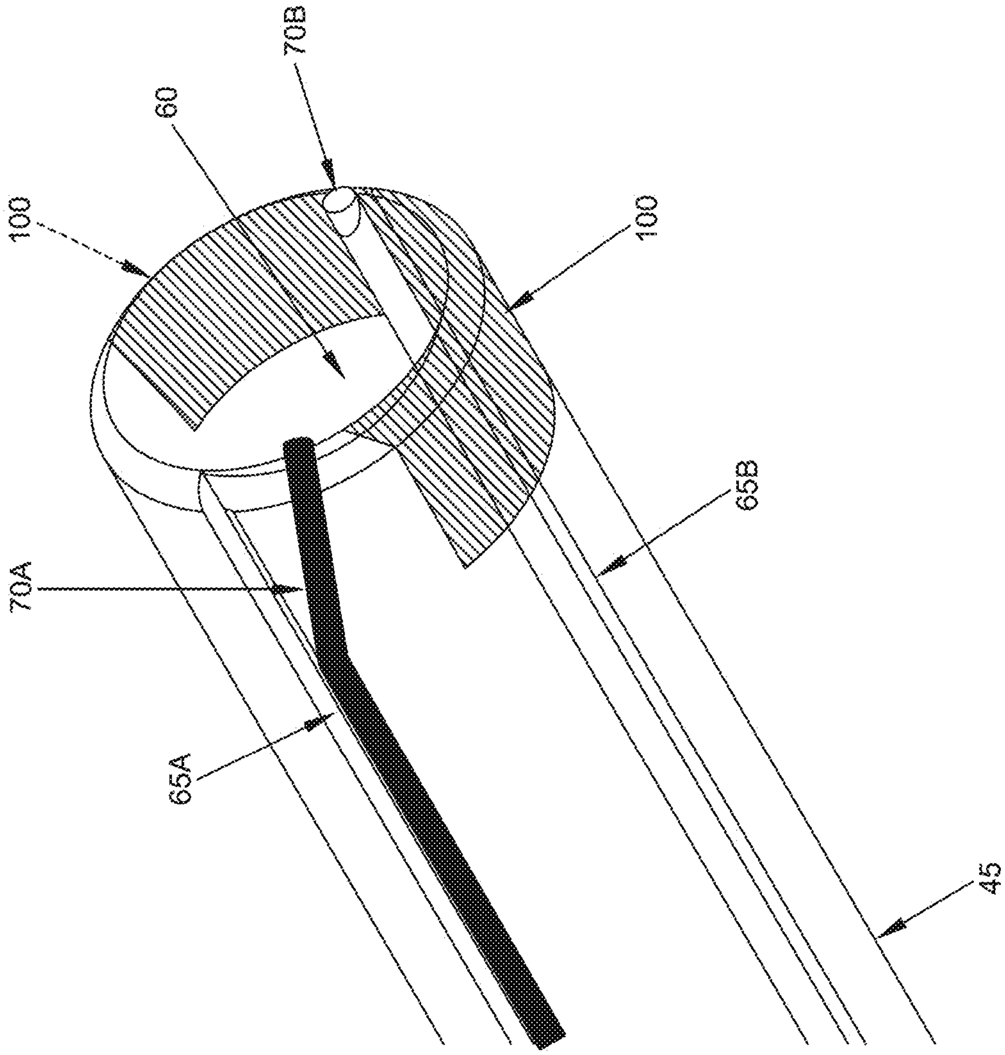
FIG. 13 is a schematic view showing another novel apparatus for evoking and sensing ophthalmic physiological signals in an eye.

Furthermore, if desired, reference electrode 70B may be "doubled over" so as to increase the surface area contact of reference electrode 70B with the eye of the mouse. And, if desired, and looking now at FIG. 13, a conductive foil (or conductive film or other conductive structure or element) 100 may be provided at distal end 50 of light pipe 45, with conductive foil (or conductive film or other conductive structure or element) 100 electrically connected to reference electrode 70B so as to increase the surface area contact of reference electrode 70B with the eye of the mouse.

Figure 14:
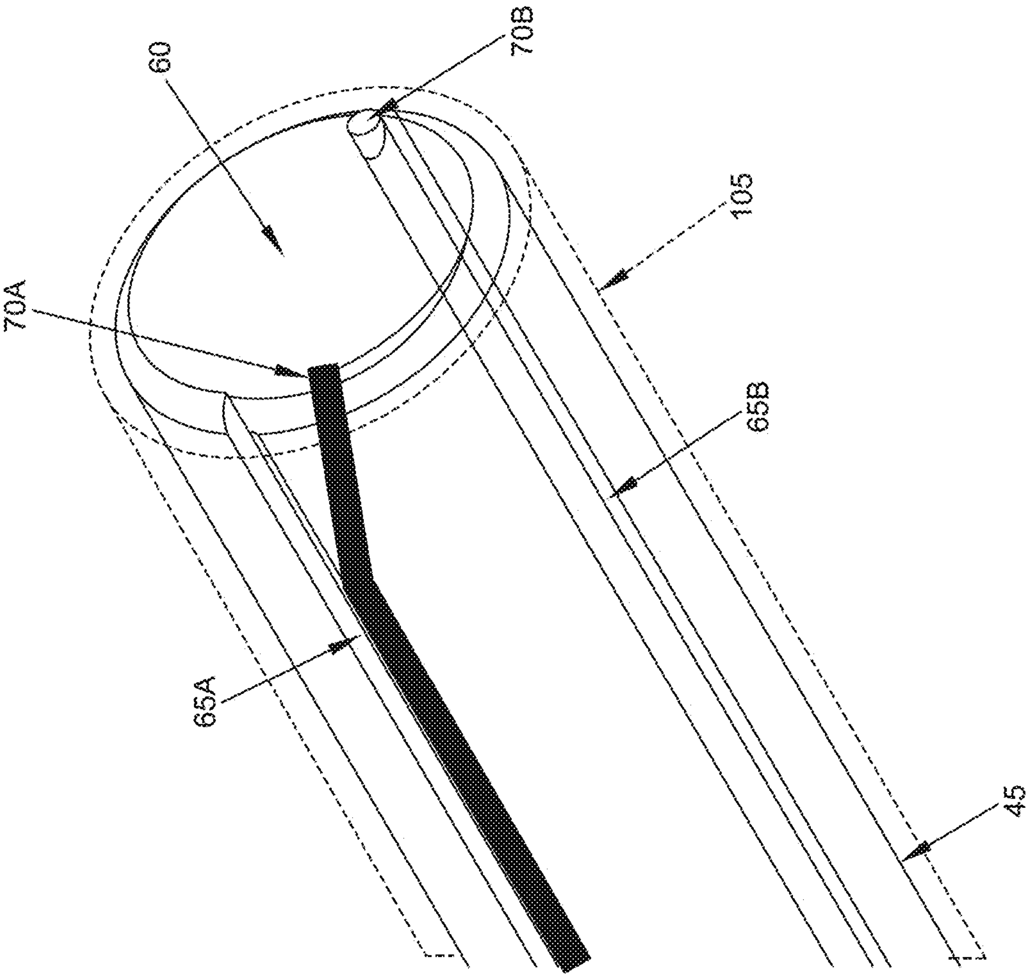
FIG. 14 is a schematic view showing still another novel apparatus for evoking and sensing ophthalmic physiological signals in an eye.

In some cases, it can be helpful to provide the user with "red light" illumination to help the user set the combined stimulator and bipolar electrode assembly 5 against the eye of the mouse. To this end, if desired, and looking now at FIG. 14, a light-transmissive sleeve 105 may be disposed coaxially about light pipe 45, with light-transmissive sleeve 105 acting as an additional light pipe for delivering red light to the distal end of light pipe 45. More particularly, in this form of the invention, when red light is introduced into the proximal end of light-transmissive sleeve 105, a ring of red light will be provided at the distal end of light-transmissive sleeve 105, whereby to provide a rim of red illuminating light about the distal perimeter of light pipe 45.

Use by Relatively Unskilled Personnel

The combined stimulator and bipolar electrode assembly 5 of the present invention can be set up much more accurately, and much more quickly, than the present state-of-the-art devices, even by relatively unskilled personnel. More particularly, after positioning the mouse on a heated table and inserting the ground electrode (e.g., in the haunch or tail of the animal), the combined stimulator and bipolar electrode assembly 5 is simply brought into contact with the eye of the mouse which is to be tested by moving housing 10 (which causes magnetic mount 40, e.g., a steel ball, to roll within a magnetic cup, e.g., a magnetic ball holder (see FIG. 1 above, which shows a magnetic ball holder of the sort which may be used), and then the test is ready to be run. A second combined stimulator and bipolar electrode assembly 5 can be used simultaneously on the fellow eye (i.e., the other eye) of the mouse if desired. This eliminates several minutes of fumbling in near darkness to carefully adjust the electrodes and position the Ganzfeld of prior art devices. Additionally, since light pipe subassembly 15 is held in position against the eye of the mouse by an external mechanical mount (i.e., magnetic mount 40) and is not supported by the eye per se, it is not necessary to use particular care to position combined stimulator and bipolar electrode assembly 5 precisely against structurally-robust eye tissue. Furthermore, since light pipe subassembly 15 has no accessible distal surface once it is seated against the eye, it is substantially impossible to obscure the light path from light pipe subassembly 15 into the eye by the use of excessive saline.

Testing of combined stimulator and bipolar electrode assembly 5 on mice has yielded excellent results. It produces expected waveforms with very little noise.

ERG Testing with the Active Electrode in One Eye and the Reference Electrode in the Other Eye Some investigators have conducted ERG testing using an active electrode in one eye of the test subject and a reference electrode in the fellow eye (i.e., the other eye) of the test subject. This technique still involves the accurate placement of two corneal wires (extremely challenging with prior art electrodes), but the fellow eye makes an excellent impedance-matched reference. However, with this approach, care must be taken to avoid light crosstalk between the eyes—the reference eye must not receive any of the stimulus light provided to the active eye.

Using the combined stimulator and bipolar electrode assembly 5 of the present invention solves both problems (i.e., accurate placement of the corneal electrode and avoiding light crosstalk between the eyes). More particularly, in one form of the invention, a first combined stimulator and bipolar electrode assembly 5 is positioned against one eye of the mouse and a second combined stimulator and bipolar electrode testing assembly 5 is positioned against the other eye of the mouse. Then the corneal electrode 70A of, for example, the right eye is plugged into the active side of the differential amplifier, and the corneal electrode 70A of the left eye is plugged into the reference side of the differential amplifier. The corneal electrodes in each eye are automatically correctly positioned by the two combined stimulator and bipolar electrode assemblies 5. The eyes of the mouse are then stimulated one at a time using the light source subassemblies 20 of the two combined stimulator and bipolar electrode assemblies 5, and there is no optical crosstalk because of the light pipe configuration (i.e., the positioning of a light pipe on an eye of the mouse limits the light reaching that eye of the mouse to only the light transmitted by that light pipe). When the right eye is being driven, the signal is normally polarized, and when the left eye is being driven, the signal is inverted.

Alternatively, both eyes of the mouse could be simultaneously stimulated using light source subassemblies 20 of the two combined stimulator and bipolar electrode assemblies 5, and the differential between the two corneal electrodes 70A may be measured so as to identify differences in eye function.

Or, if desired, the reference electrodes 70B may be used in place of the corneal electrodes 70A (assuming, of course, that the reference electrodes 70B are in contact with portions of the eyes which exhibit evoked physiological signals). In this form of the invention, the reference electrode 70B of, for example, the right eye is plugged into the active side of the differential amplifier, and the reference electrode 70B of the left eye is plugged into the reference side of the differential amplifier. The reference electrodes in each eye are automatically correctly positioned by the two combined stimulator and bipolar electrode assemblies 5. The eyes are then stimulated one at a time using the light source subassemblies 20 of the combined stimulator and bipolar electrode assemblies 5, and there is no optical crosstalk because of the light pipe configuration (i.e., the positioning of a light pipe on an eye of the mouse limits the light reaching that eye of the mouse to only the light transmitted by that light pipe). When the right eye is being driven, the signal is correctly polarized, and when the left eye is being driven, the signal is inverted.

Alternatively, both eyes of the mouse may be simultaneously stimulated using light source subassemblies 20 of the combined stimulator and bipolar electrode assemblies 5, and the differential between the two reference electrodes 70B may be measured so as to identify differences in eye function.

Significantly, where two combined stimulator and bipolar electrode assemblies 5 are positioned against both eyes of the mouse, and where a single differential amplifier is used to measure the evoked physiological signal (i.e., where an electrode 70A or 70B from one combined stimulator and bipolar electrode assembly 5 is plugged into the active side of the differential amplifier and the corresponding electrode 70A or 70B from the other combined stimulator and bipolar electrode assembly 5 is plugged into the reference side of the differential amplifier), and where the active and reference sides of the differential amplifier share a common rail, it can be possible to omit the aforementioned ground electrode entirely, with the evoked physiological signal being measured using just the two electrodes from the two combined stimulator and bipolar electrode assemblies. This feature has significant clinical advantage, since testing can be effected by simply bringing the two combined stimulator and bipolar electrode assemblies into contact with the two eyes of the mouse and then commencing testing, without requiring attachment of the ground electrode to the haunch or tail of the mouse, thereby greatly speeding up testing time.

Combined Stimulator and Monopolar Electrode Assembly

Figure 15:
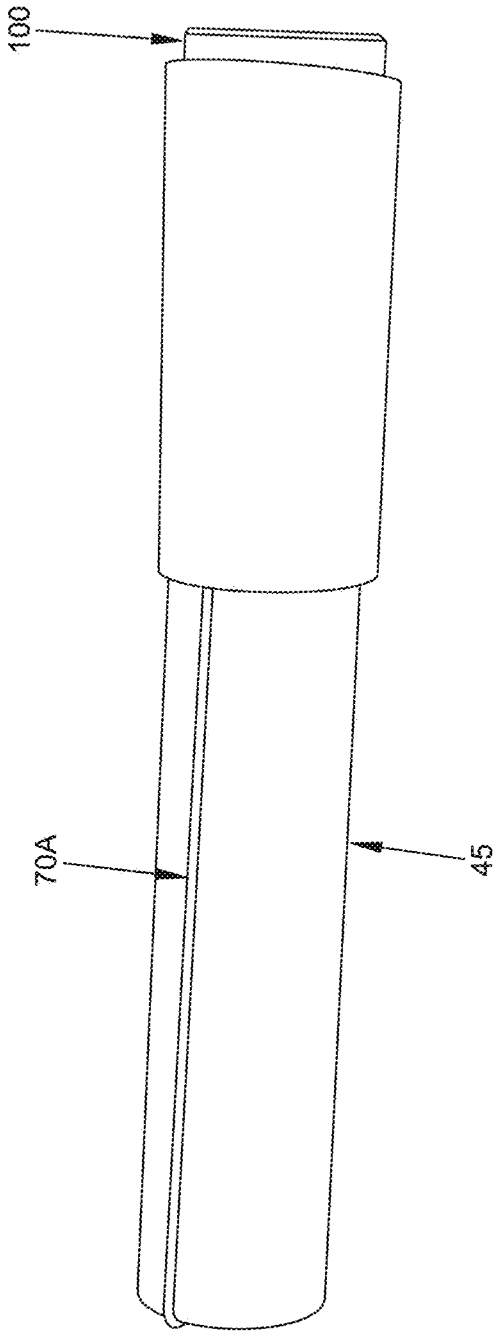
FIGS. 15-17 are schematic views showing yet another novel apparatus for evoking and sensing ophthalmic physiological signals in an eye.
Figure 16:
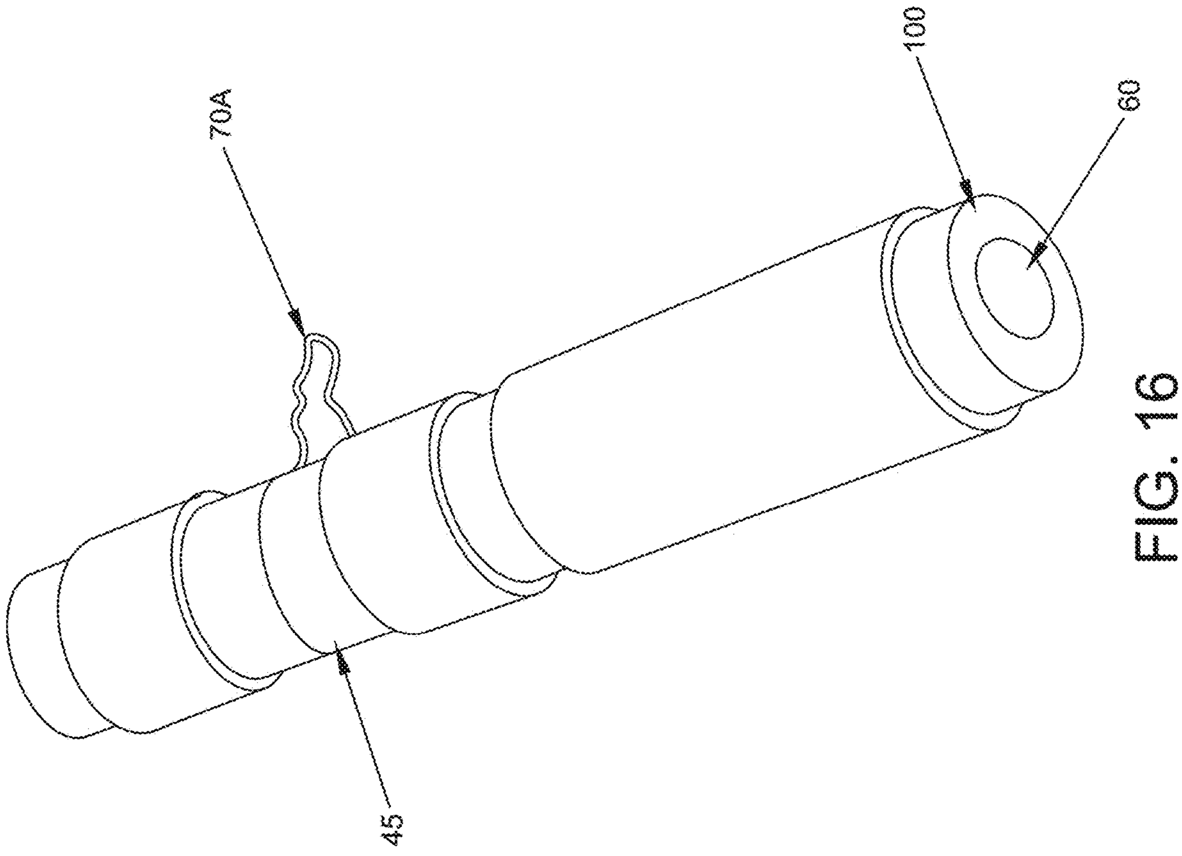
Figure 17:
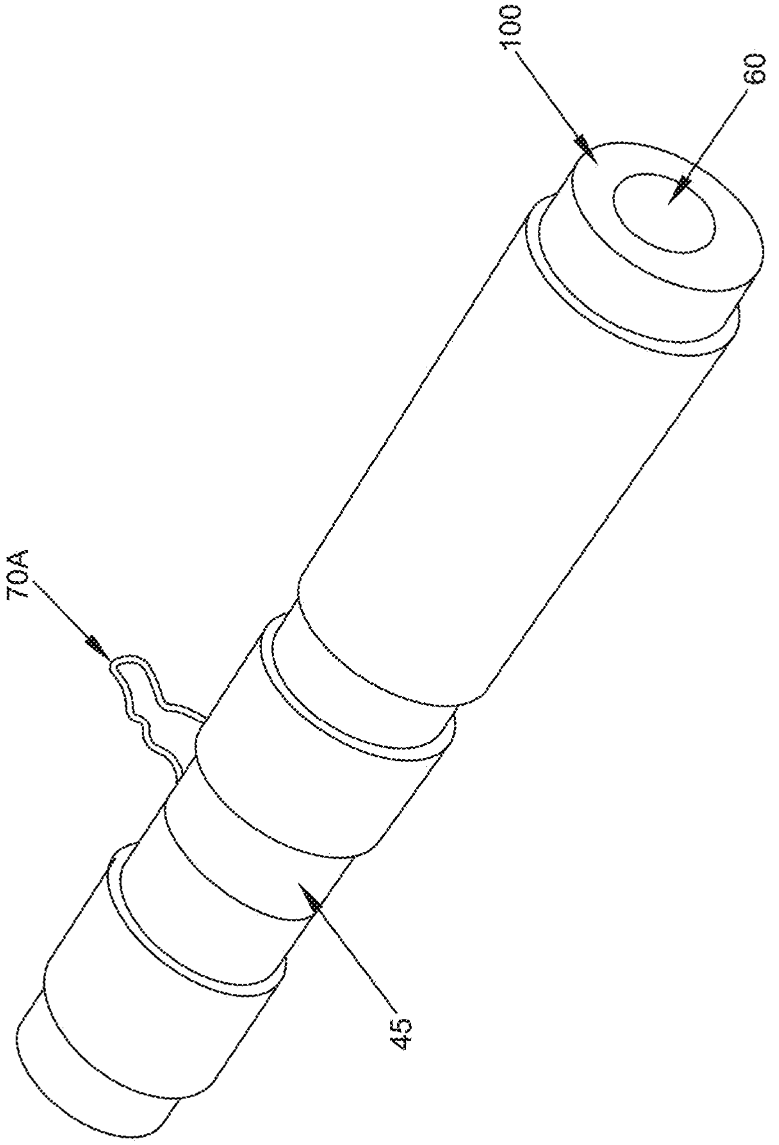
Figure 19:
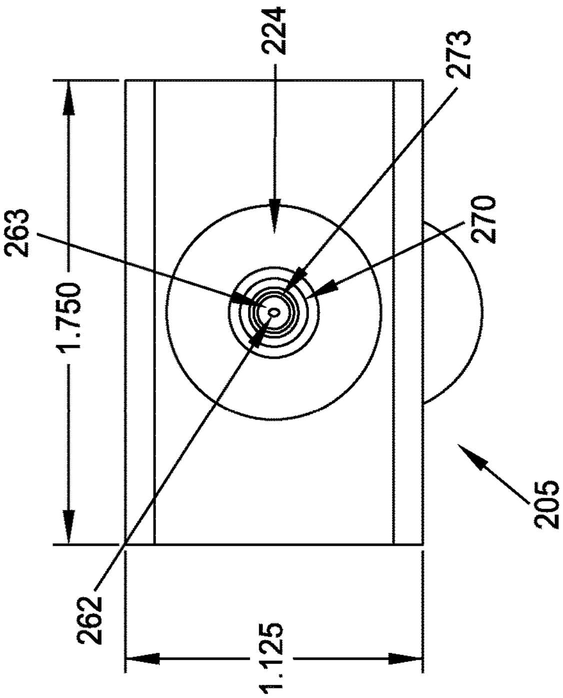
FIGS. 18-22 are schematic views showing still another novel apparatus for evoking and sensing ophthalmic physiological signals in an eye.
Figure 18:
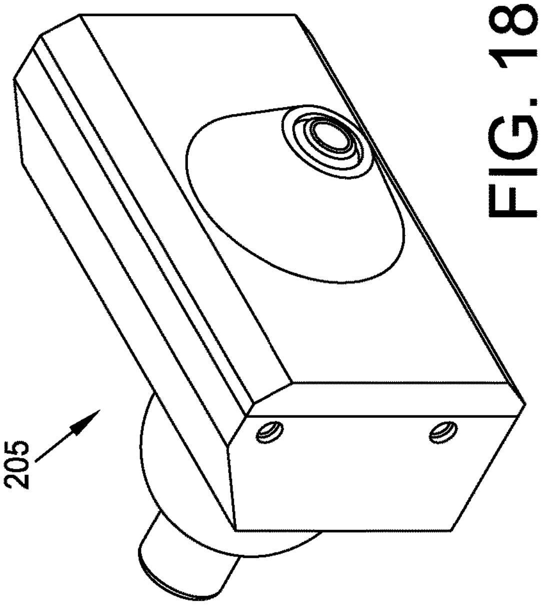
Figure 20:
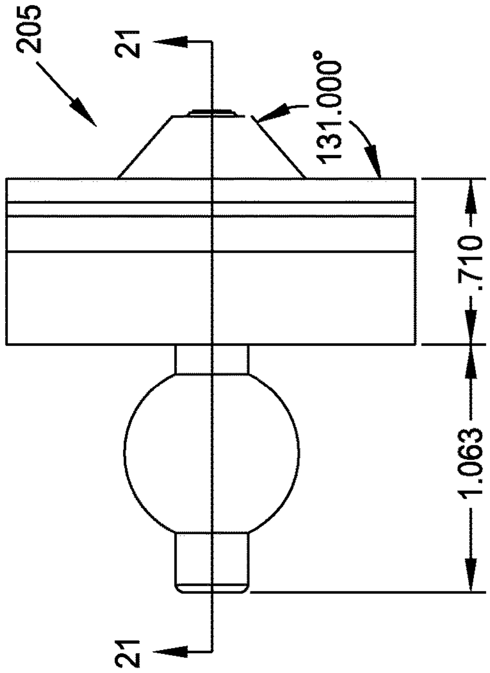
Figure 21:
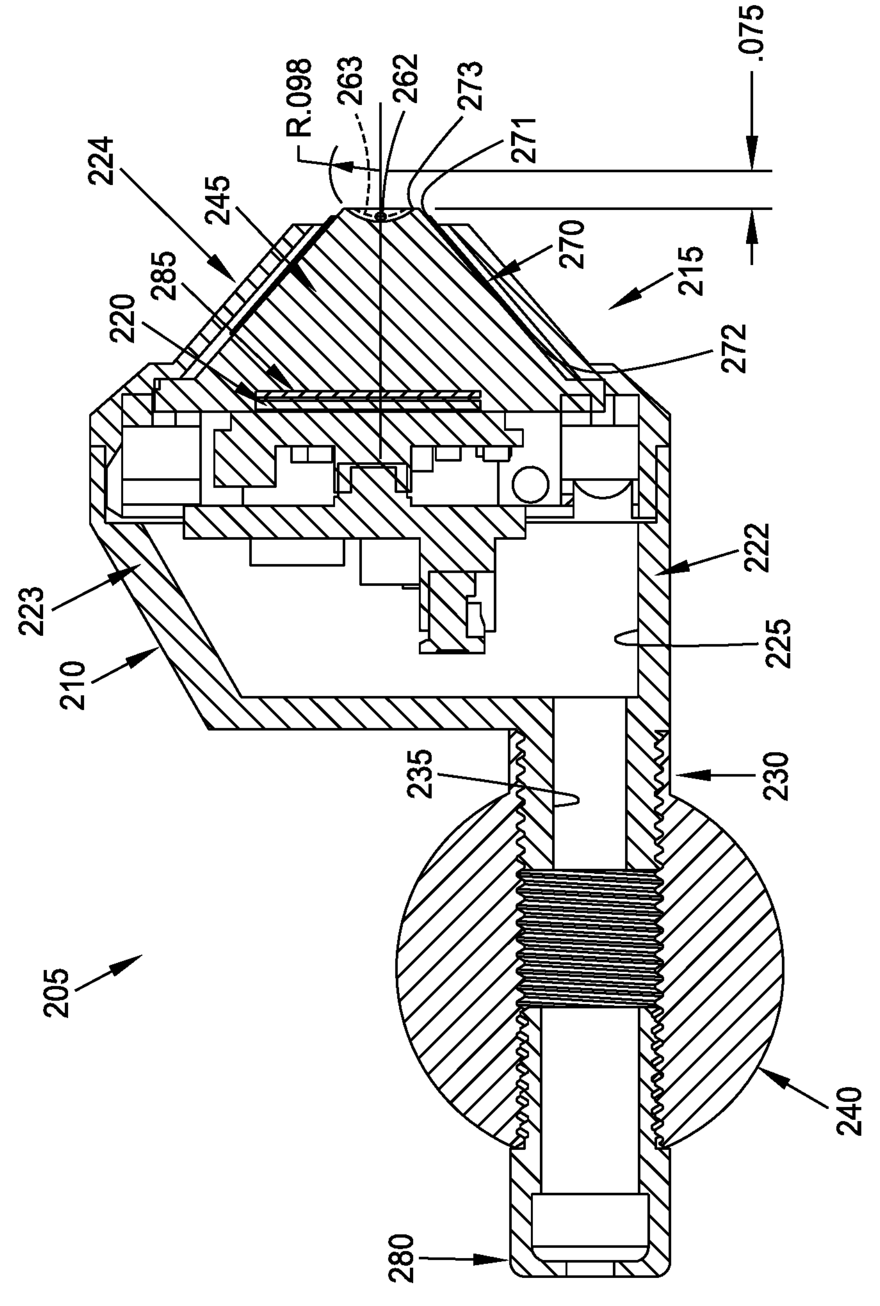
Figure 22:
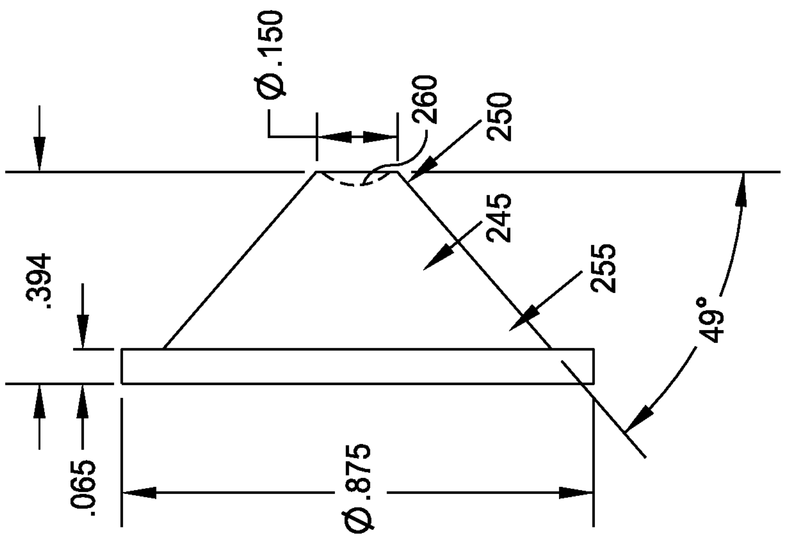

In one preferred form of the invention, and looking now at FIGS. 15-17, platinum wire 70A can be omitted and platinum wire 70B can be provided with a conductive foil (or conductive film or other conductive structure or element) 100, e.g., formed out of silver/silver chloride, where conductive foil (or conductive film or other conductive structure or element) 100 preferably extends around substantially the complete perimeter of distal end 50 of light pipe 45. When configured in this manner, the present invention essentially comprises a combined stimulator and monopolar electrode assembly (since only one electrode, i.e., electrode 70B/conductive foil (or conductive film or other conductive structure or element) 100, is provided). This form of the invention can be advantageous where two combined stimulator and monopolar electrode assemblies 5 are positioned against both eyes of the mouse and one eye provides one signal and the other eye provides another signal (e.g., for stimulating one eye at a time, where one eye provides the active signal and the other eye provides the reference signal, or for simultaneously stimulating both eyes at the same time, where each eye provides an active signal).

Again, where two combined stimulator and monopolar electrode assemblies 5 are positioned against both eyes of the mouse, and where a single differential amplifier is used to measure the evoked physiological signal (i.e., where an electrode 70B from one combined stimulator and monopolar electrode assembly 5 is plugged into the active side of the differential amplifier and the corresponding electrode 70B from the other combined stimulator and monopolar electrode assembly 5 is plugged into the reference side of the differential amplifier), and where the active and reference sides of the differential amplifier share a common rail, it can be possible to omit the aforementioned ground electrode entirely, with the evoked physiological signal being measured using just the two electrodes from the two combined stimulator and monopolar electrode assemblies. Again, this feature has significant clinical advantage, since testing can be effected by simply bringing the two combined stimulator and monopolar electrode assemblies into contact with the two eyes of the mouse and then commencing testing, without requiring attachment of the ground electrode to the haunch or tail of the mouse, thereby greatly speeding up testing time.

Robustness of the Electrical and Optical Connections

The robustness of the electrical and optical connections that the new combined stimulator and bipolar (or monopolar) electrode assembly 5 makes with the eye of the mouse has been dramatically demonstrated during testing. Toward the end of testing, the mice may wake up and begin to move. With conventional setups, the first movement of the awakening mouse breaks corneal contact and the testing is over. With the combined stimulator and bipolar electrode assembly 5 of the present invention, contact with the awakening mouse was successfully maintained even though the mouse was moving and testing continued with good results until the mouse literally walked away from the testing platform.

Positioning the Electrode Wires within the Light Pipe

In the foregoing disclosure, platinum wire 70A (i.e., the active electrode) is disposed within slot 65A which extends along an outer surface of light pipe 45, and platinum wire 70B (i.e., the reference electrode) is disposed within slot 65B which extends along an outer surface of light pipe 45. However, if desired, slot 65A could be replaced with a bore extending longitudinally through light pipe 45 and platinum wire 70A (i.e., the active electrode) may be disposed within this longitudinal bore; and/or slot 65B could be replaced with a bore extending longitudinally through light pipe 45 and platinum wire 70B (i.e., the reference electrode) may be disposed within this other longitudinal bore. In such a construction, the longitudinal bore receiving platinum wire 70A (i.e., the active electrode) is disposed closer to the longitudinal axis of light pipe 45 than the longitudinal bore receiving platinum wire 70B (i.e., the reference electrode).

Glaucoma and Pattern Electroretinograms (Pattern ERGs)

When a test subject is to be tested for glaucoma, a pattern stimulus (e.g., alternating light and dark horizontal bars, or gratings, or checkerboard patterns, etc.) is presented to the retina of an eye of the test subject and the electrophysiological response of the retina is measured. This is commonly referred to as a pattern electroretinogram (pattern ERG). Glaucoma damages the ganglion cells in the retina and causes a reduced retina response which can be detected from the pattern ERG. Therefore, pattern ERGs are valuable tools for assessing the presence, and extent, of glaucoma in a test subject.

The pattern ERG is a very small response which is difficult to elicit or measure even in humans, and in mice it is especially difficult. The most successful attempts in mice have been made by very experienced researchers who use microscopic thread electrodes to measure the voltage at the surface of the eye. Small mouse-sized contact lenses are placed over the electrode to hydrate the cornea and prevent cataracts (which otherwise form quickly in mice and prevent them from seeing the pattern stimulus). The contact lens also preserves the optical properties of the cornea, which otherwise would be degraded by the tear film that builds up around an electrode that simply touches the cornea. The pattern stimulus is generally produced on a cathode ray tube (CRT), which is a bulky, obsolete technology that is nevertheless necessary in order to avoid the flash artifact (also sometimes referred to as the luminance artifact) produced by all liquid crystal display (LCD) screens and even most modern OLED screens. The flash artifact is an overall screen luminance change that occurs during the frame in which the dark bars are turning light and vice versa. This flash artifact destroys the pattern ERG response by creating a much larger flash response that overwhelms the pattern ERG response.

Many researchers who need to perform pattern ERGs are not in a position to invest the substantial time required to learn this difficult technique.

The present invention provides a new and improved approach for quickly and easily performing pattern ERGs on mice. Among other things, the present invention dramatically reduces the time needed to set up and measure the pattern ERG in rodents, and eliminates the necessity of manipulating mouse-sized contact lenses.

Combined Pattern Stimulator and Monopolar Electrode Assembly

In one form of the invention, and looking now at FIGS. 18-22, there is provided a combined pattern stimulator and monopolar electrode assembly 205. Combined pattern stimulator and monopolar electrode assembly 205 generally comprises a housing 210, a light pipe subassembly 215 and a light source subassembly 220.

Housing 210 preferably comprises a main body 222 having a cavity 225 formed therein, and a rear arm 230 extending rearwardly from main body 222. If desired, main body 222 may comprise a rear portion 223 and a front portion 224. Rear arm 230 includes a cavity 235 formed therein, and a magnetic mount 240 (preferably in the form of a steel ball) secured to (or formed integral with) rear arm 230.

Light pipe subassembly 215 is disposed partially within, and protrudes from, cavity 225 of main body 222. Light pipe subassembly 215 generally comprises a light pipe 245 formed out of a light-transmissive material (e.g., Plexiglas or other acrylic, Lexan or other polycarbonate, or glass, etc.). Light pipe 245 has a distal end 250 and a proximal end 255. Light pipe 245 has an elongated configuration, and is preferably tapered (e.g., conical or frustoconical), with its distal end 250 being approximately the size of an eye of a mouse and its proximal end 255 being approximately the size of the pattern stimulator (see below) of light source subassembly 220. Distal end 250 of light pipe 245 has a spheroidal recess 260 formed therein. The radius of curvature of spheroidal recess 260 is preferably similar to the radius of curvature of the eye of a mouse, so that distal end 250 of light pipe 245 can be seated against the outside surface of the eye of a mouse.

A pinhole aperture 262 is formed on the surface of spheroidal recess 260 so as to act as a lens for an optical image passing down light pipe 245 (see below). Pinhole aperture 262 may be formed by depositing an opaque material 263 (e.g., a layer of opaque paint, or titanium nitride, or polyvinylchloride PVC, etc.) on the surface of spheroidal recess 260.

Light pipe 245 also comprises a platinum (or silver or gold, etc.) electrode 270 disposed on the sidewall of light pipe 245. Electrode 270 preferably comprises a distal ring 271 and a pair of wires 272 which extend proximally from distal ring 271. Note that distal ring 271 of electrode 270 sits just proximal to the peripheral rim 273 of spheroidal recess 260, so that when light pipe 245 is brought into contact with the eye of a mouse, distal ring 271 of electrode 270 will make secure contact with tissue of the eye which exhibits an evoked physiological signal.

The wires 272 of electrode 270 extend through cavity 225 of main body 220 and through cavity 235 of rear arm 230 so that they can be brought out the proximal end 280 of rear arm 230 for connection to appropriate amplification (e.g., by a differential amplifier) and processing electronics (not shown) for ERG signal processing.

Light source subassembly 220 is disposed within cavity 225 of main body 220. Light source subassembly 220 generally comprises light-emitting diodes (LEDs or OLEDs) 285 for generating a pattern of light (e.g., alternating light and dark horizontal bars, or gratings, or checkerboard patterns, etc.), and any appropriate optics (not shown) required to transmit the light pattern generated by LEDs 285 into the proximal end 255 of light pipe 245, whereupon the light pattern will travel down the length of light pipe 245 to the distal end 250 of light pipe 245. In one preferred form of the invention, LEDs 285 comprise an organic light-emitting diode (OLED) display of the sort which does not produce the aforementioned flash artifact. A power line (not shown) passes through cavity 235 of rear arm 230 and cavity 225 of main body 220 to provide power to LEDs 285.

When a mouse is to be tested for PERG (e.g., for glaucoma models), the mouse is placed on an appropriate platform, a ground electrode (not shown) is attached to the mouse (e.g., in the haunch or tail of the animal), and then a first combined pattern stimulator and monopolar electrode assembly 205 is brought into contact with one eye of the mouse (i.e., so as to bring distal end 250 of light pipe 245 into contact with the eye of the mouse, with pinhole aperture 262 being directed into the eye of the mouse and with distal ring 271 of electrode 270 appropriately engaging the eye of the mouse), and a second combined pattern generator and monopolar electrode assembly 205 is brought into contact with the second eye of the mouse (i.e., in a manner analogous to how the first combined pattern stimulator and monopolar electrode assembly 205 is brought into contact with the eye of the mouse). Preferably the spheroidal recesses 260 of the combined pattern stimulator and monopolar electrode assemblies 205 are wetted with an isotonic saline solution prior to bringing the assemblies into contact with the eyes of the mouse. When LEDs 285 of the first combined pattern stimulator and monopolar electrode assembly 205 are thereafter energized, the light pattern from LEDs 285 passes down light pipe 245 and into the eye of the mouse, whereby to stimulate the eye of the mouse. Note that pinhole aperture 262 on the surface of spheroidal recess 260 focuses the light pattern on the retina of the mouse, so that the retina of the mouse receives the stimulation pattern necessary to perform pattern ERG. The electrode 270 from that first combined pattern stimulator and monopolar electrode assembly 205 acts as the active electrode and the electrode 270 from the second combined pattern stimulator and monopolar electrode assembly 205 acts as the reference electrode so as to pick up the electrophysiological response of the eye of the mouse as electrical signals, and these electrical signals are passed to appropriate amplification and processing electronics for ERG signal processing.

Thus it will be seen that a pair of combined pattern stimulator and monopolar electrode assemblies 205 may be brought into contact with the two eyes of a mouse, one of the combined pattern generators and monopolar electrode assemblies 205 may be energized so as to project the desired light pattern (with no luminance artifact) on one eye of the mouse, the electrode 270 of that combined pattern stimulator and monopolar assembly 205 may be used as the active electrode and the electrode 270 of the other combined pattern generator and monopolar electrode assembly may be used as the reference electrode, whereby to perform pattern ERG on the mouse.

Note that when the combined pattern stimulator and monopolar electrode assembly 205 contacts the eye of a mouse, spheroidal recess 260 of light pipe 245 covers the eye of the mouse so as to prevent dehydration of the cornea.

Note also that distal ring 271 of electrode 270 contacts the tear film of the eye so as to provide an excellent electrical contact.

And, again, because the pattern ERG testing uses an active electrode on one eye of the test subject and a reference electrode on the fellow eye (i.e., the other eye) of the test subject, there is excellent impedance-matching between the active electrode and the reference electrode. And there is no optical crosstalk between the eyes because of the light pipe configuration (i.e., the positioning of a light pipe on an eye of the mouse limits the light reaching that eye of the mouse to only the light transmitted by that light pipe).

Again, where two combined pattern stimulator and monopolar electrode assemblies 205 are positioned against both eyes of the mouse, and where a single differential amplifier is used to measure the evoked physiological signal (i.e., where an electrode 270 from one combined pattern stimulator and monopolar electrode assembly 205 is plugged into the active side of the differential amplifier and the corresponding electrode 270 from the other combined pattern stimulator and monopolar electrode assembly 205 is plugged into the reference side of the differential amplifier), and where the active and reference sides of the differential amplifier share a common rail, it can be possible to omit the aforementioned ground electrode entirely, with the evoked physiological signal being measured using just the two electrodes from the two combined pattern stimulator and monopolar electrode assemblies 205. Again, this feature has significant clinical advantage, since testing can be effected by simply bringing the two combined pattern stimulator and monopolar electrode assemblies into contact with the two eyes of the mouse and then commencing testing, without requiring attachment of the ground electrode to the haunch or tail of the mouse, thereby greatly speeding up testing time.

Figure 23:
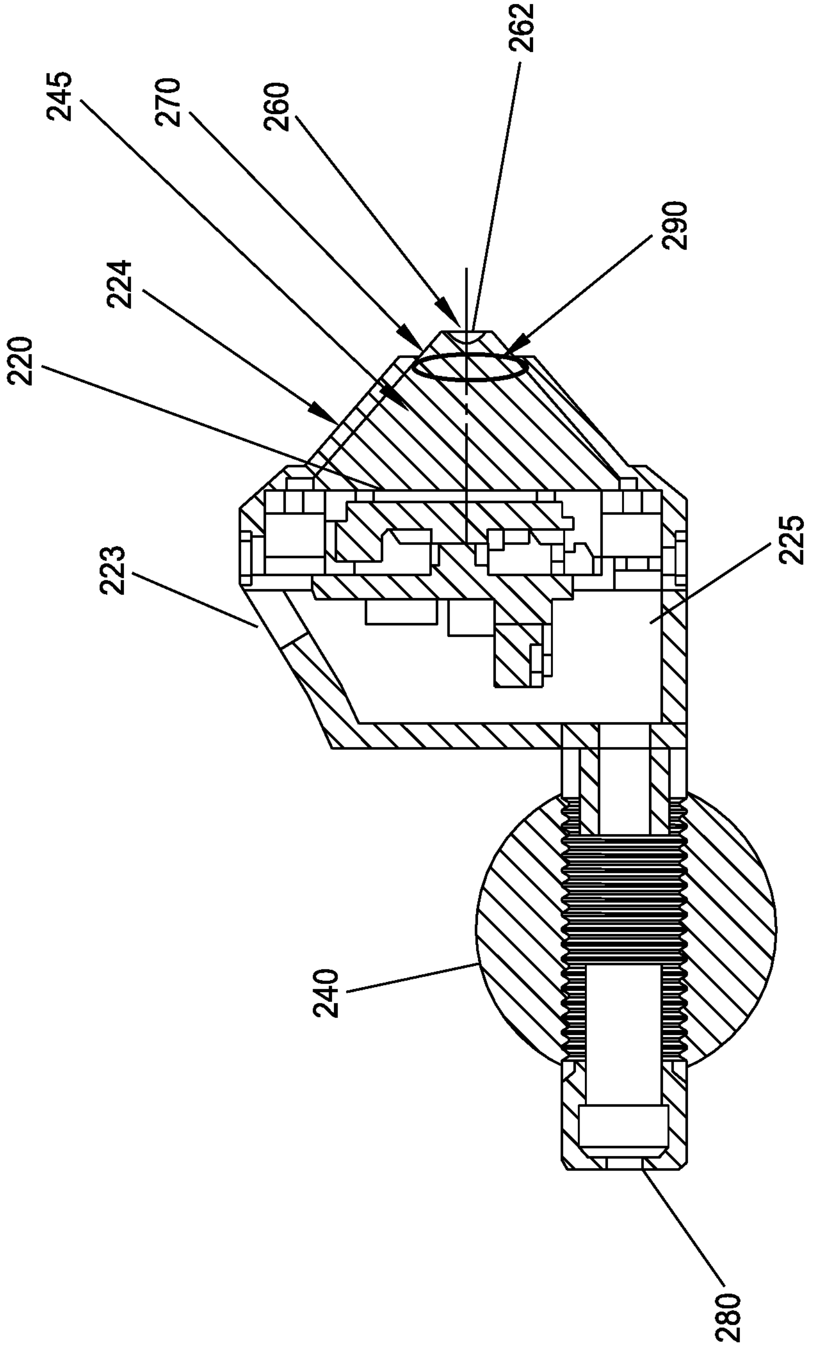
FIG. 23 is a schematic view showing another novel apparatus for evoking and sensing ophthalmic physiological signals in an eye.
Figure 27:
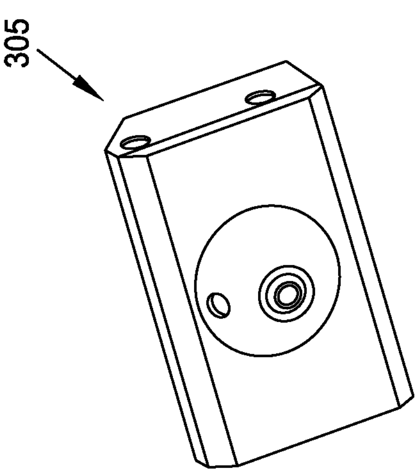
FIGS. 24-29 are schematic views showing another novel apparatus for evoking and sensing ophthalmic physiological signals in an eye.
Figure 26:
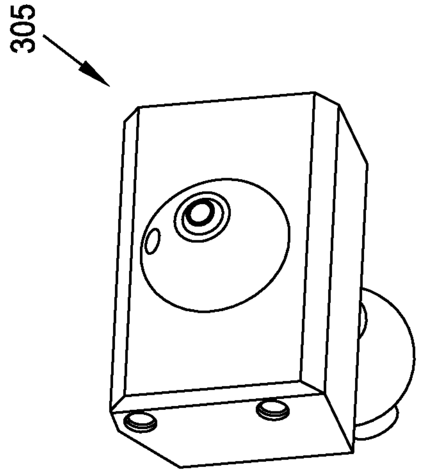
Figure 24:
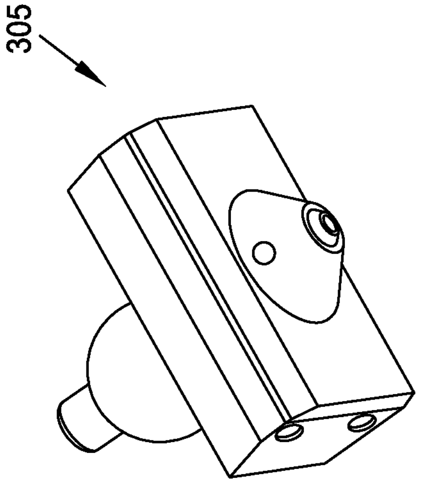
Figure 25:
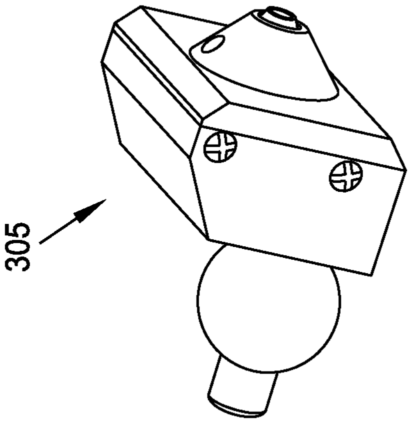
Figure 28:
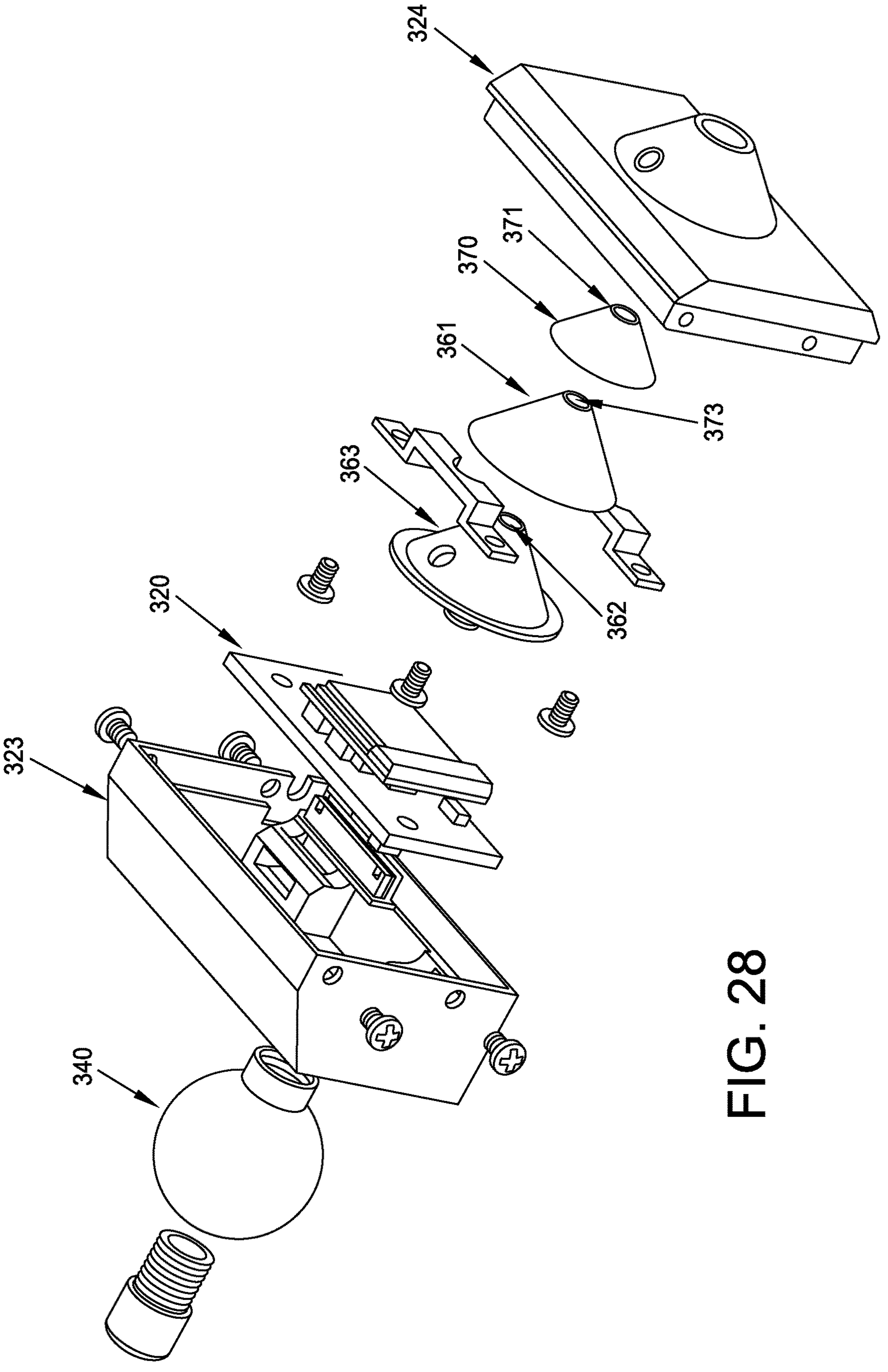
Figure 29:
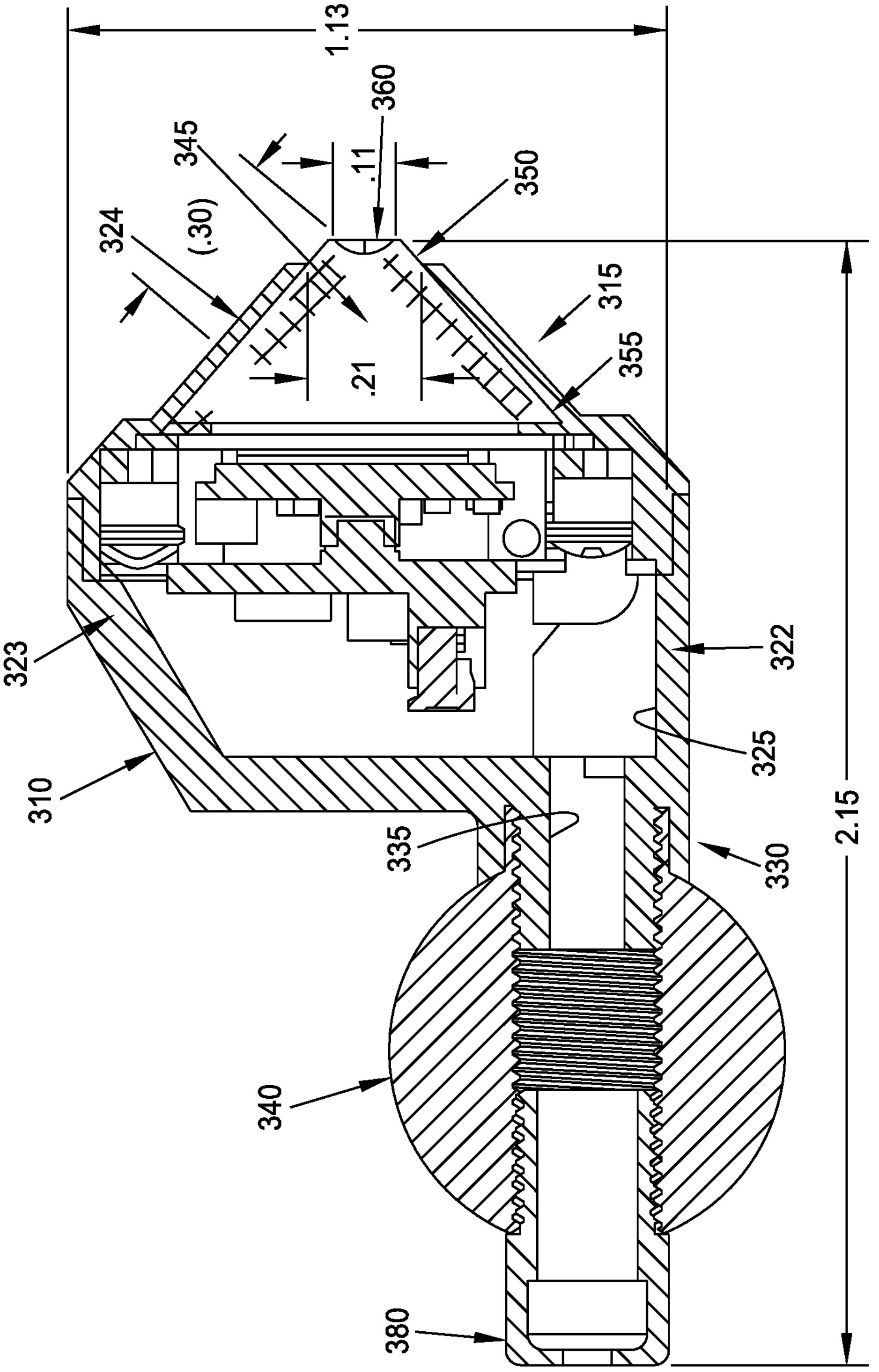

FIG. 23 shows another combined pattern stimulator and monopolar electrode assembly 205. The combined pattern stimulator and monopolar electrode assembly shown in FIG. 23 is substantially identical to the combined pattern stimulator and monopolar electrode assembly 205 shown in FIGS. 18-22, except that pinhole aperture 262 and opaque material 263 (which together serve as a lens to focus the pattern image passing down light pipe 245 on the retina of an eye) is replaced by an optical refracting lens 290.

Note that a pattern stimulator (i.e., a combined pattern stimulator and monopolar electrode assembly 205) may be used in one eye and a Ganzfeld stimulator (i.e., a combined stimulator and bipolar/monopolar electrode assembly 5) may be used for the other eye (but note that where the Ganzfeld stimulator comprises a combined stimulator and bipolar electrode assembly 5, only one electrode 70A or 70B is used for detecting an evoked physiological signal, since the other electrode is provided by the combined pattern stimulator and monopolar electrode assembly 205).

FIGS. 24-29 show another combined pattern stimulator and monopolar electrode assembly 305. The combined pattern stimulator and monopolar electrode assembly 305 shown in FIGS. 24-29 is similar to the combined pattern stimulator and monopolar electrode assembly 205 shown in FIGS. 18-22, and to the combined pattern stimulator and monopolar electrode assembly 205 shown in FIG. 23, except that the tapered (e.g., conical or frustoconical) Plexiglas (or other acrylic, or Lexan or other polycarbonate, or glass, etc.) light pipe 245 of the constructions shown in FIGS. 18-22 and FIG. 23 are replaced by a light pipe which is essentially an air-filled spacer.

More particularly, in this form of the invention, combined pattern stimulator and monopolar electrode assembly 305 generally comprises a housing 310, a light pipe subassembly 315 and a light source subassembly 320.

Housing 310 preferably comprises a main body 322 having a cavity 325 formed therein, and a rear arm 330 extending rearwardly from main body 322. If desired, main body 322 may comprise a rear portion 323 and a front portion 324. Rear arm 330 includes a cavity 335 formed therein, and a magnetic mount 340 (preferably in the form of a steel ball) secured to (or formed integral with) rear arm 330.

Light pipe subassembly 315 is disposed partially within, and protrudes from, cavity 325 of main body 322. Light pipe subassembly 315 generally comprises a light pipe 345 which is essentially an air-filled spacer having a distal end 350 and a proximal end 355. Light pipe 345 has an elongated configuration, and is preferably tapered (e.g., conical or frustoconical), with its distal end 350 being approximately the size of an eye of a mouse and its proximal end 355 being approximately the size of the pattern stimulator (see below) of light source subassembly 320. Distal end 350 of light pipe 345 has a spheroidal recess 360 formed therein. The radius of curvature of spheroidal recess 360 is preferably similar to the radius of curvature of the eye of a mouse, so that distal end 350 of light pipe 345 can be seated against the outside surface of the eye of a mouse.

In one preferred form of the invention, light pipe 345 comprises (i) a transparent plastic cone 361 which comprises the aforementioned spheroidal recess 360, and (ii) an opaque plastic cone 363. The exterior of opaque plastic cone 363 preferably seats against the interior of transparent plastic cone 361, with transparent plastic cone 361 and opaque plastic cone 363 together providing a generally tapered (e.g., conical or frustoconical) configuration for light pipe 345. It will be appreciated that light pipe 345 is filled with air, which is a light-transmissive material, such that light entering proximal end 355 of light pipe 345 is transmitted to distal end 350 of light pipe 345, where it emerges from spheroidal recess 360.

In one preferred form of the invention, light pipe 345 also comprises a pinhole aperture which acts as a lens for an optical image passing down light pipe 345. In one preferred form of the invention, the pinhole aperture is provided by forming a pinhole aperture 362 at the apex of opaque plastic cone 363. It will be appreciated that because the thin material between the mouse's eye and the hollow portion of the cone essentially comprises a zero power contact lens, the pinhole aperture is not strictly necessary and may be omitted to provide increased illumination, especially with larger animals.

Light pipe 345 also comprises a platinum (or silver or gold, etc.) electrode 370 disposed on the front side of light pipe 345. In one preferred form of the invention, electrode 370 comprises a silver cone which terminates in a distal rim 371, and a pair of wires (not shown) which extend proximally from the silver cone. Note that distal rim 371 of electrode 370 sits just proximal to the peripheral rim 373 of spheroidal recess 360, so that when light pipe 345 is brought into contact with the eye of a mouse, distal rim 371 of electrode 370 will make secure contact with tissue of the eye which exhibits an evoked physiological signal.

The wires (not shown) of electrode 370 extend through cavity 325 of main body 320 and through cavity 335 of rear arm 330 so that the wires can be brought out the proximal end 380 of rear arm 330 for connection to appropriate amplification (e.g., by a differential amplifier) and processing electronics (not shown) for ERG signal processing.

Light source subassembly 320 is disposed within cavity 325 of main body 320. Light source subassembly 320 generally comprises light-emitting diodes (LEDs) for generating a pattern of light (e.g., alternating light and dark horizontal bars, or gratings, or checkerboard patterns, etc.), and any appropriate optics (not shown) required to transmit the light pattern generated by the LEDs into the proximal end 355 of light pipe 345, whereupon the light pattern will travel down the length of light pipe 345 to the distal end 350 of light pipe 345. In one preferred form of the invention, the LEDs comprise an organic light-emitting diode (OLED) display of the sort which does not produce the aforementioned flash artifact. A power and control line (not shown) passes through cavity 335 of rear arm 330 and cavity 325 of main body 320 to provide power and control signals to the LEDs.

When a mouse is to be tested using a pattern stimulator, the mouse is placed on an appropriate platform, a ground electrode (not shown) is attached to the mouse (e.g., in the haunch or tail of the animal), and then a first combined pattern stimulator and monopolar electrode assembly 305 is brought into contact with one eye of the mouse (i.e., so as to bring distal end 350 of light pipe 345 into contact with the eye of the mouse, with pinhole aperture 362 being directed into the eye of the mouse and with distal rim 371 of electrode 370 appropriately engaging the eye of the mouse), and a second combined pattern generator and monopolar electrode assembly 305 is brought into contact with the second eye of the mouse (i.e., in a manner analogous to how the first combined pattern stimulator and monopolar electrode assembly 305 is brought into contact with the eye of the mouse). Preferably the spheroidal recesses 360 of the combined pattern stimulator and monopolar electrode assemblies 305 are wetted with an isotonic saline solution prior to bringing the assemblies into contact with the eyes of the mouse. When the LEDs of the first combined pattern stimulator and monopolar electrode assembly 305 are thereafter energized, the light pattern from the LEDs passes down light pipe 345 and into the eye of the mouse, whereby to stimulate the eye of the mouse. Note that pinhole aperture 362 on the surface of spheroidal recess 360 helps focus the light pattern on the retina of the mouse, so that the retina of the mouse receives the stimulation pattern necessary to perform pattern ERG, pattern visual evoked potential (VEP), or multi-focal ERG and VEP. The electrode 370 from that first combined pattern stimulator and monopolar electrode assembly 305 acts as the active electrode and the electrode 370 from the second combined pattern stimulator and monopolar electrode assembly 305 acts as the reference electrode so as to pick up the electrophysiological response of the eye of the mouse as electrical signals, and these electrical signals are passed to appropriate amplification and processing electronics for ERG signal processing.

Thus it will be seen that a pair of combined pattern stimulator and monopolar electrode assemblies 305 may be brought into contact with the two eyes of a mouse, one of the combined pattern stimulators and monopolar electrode assemblies 305 may be energized so as to project the desired light pattern (with no luminance artifact) on one eye of the mouse, the electrode 370 of that combined pattern stimulator and monopolar assembly 305 may be used as the active electrode and the electrode 370 of the other combined pattern stimulator and monopolar electrode assembly may be used as the reference electrode, whereby to perform pattern ERG on the mouse.

Note that when the combined pattern stimulator and monopolar electrode assembly 305 contacts the eye of a mouse, spheroidal recess 360 of light pipe 345 covers the eye of the mouse so as to prevent dehydration of the cornea.

Note also that distal rim 371 of electrode 370 contacts the tear film of the eye so as to provide an excellent electrical contact.

And, again, because the pattern ERG testing uses an active electrode on one eye of the test subject and a reference electrode on the fellow eye (i.e., the other eye) of the test subject, there is excellent impedance-matching between the active electrode and the reference electrode. And there is no optical crosstalk between the eyes because of the light pipe configuration (i.e., the positioning of a light pipe on an eye of the mouse limits the light reaching that eye of the mouse to only the light transmitted by that light pipe).

And again, where two combined pattern stimulator and monopolar electrode assemblies 305 are positioned against both eyes of the mouse, and where a single differential amplifier is used to measure the evoked physiological signal (i.e., where an electrode 370 from one combined pattern stimulator and monopolar electrode assembly 305 is plugged into the active side of the differential amplifier and the corresponding electrode 370 from the other combined pattern stimulator and monopolar electrode assembly 305 is plugged into the reference side of the differential amplifier), and where the active and reference sides of the differential amplifier share a common rail, it can be possible to omit the aforementioned ground electrode entirely, with the evoked physiological signal being measured using just the two electrodes from the two combined pattern stimulator and monopolar electrode assemblies 305. Again, this feature has significant clinical advantage, since testing can be effected by simply bringing the two combined pattern stimulator and monopolar electrode assemblies into contact with the two eyes of the mouse and then commencing testing, without requiring attachment of the ground electrode to the haunch or tail of the mouse, thereby greatly speeding up testing time.

Figure 30:
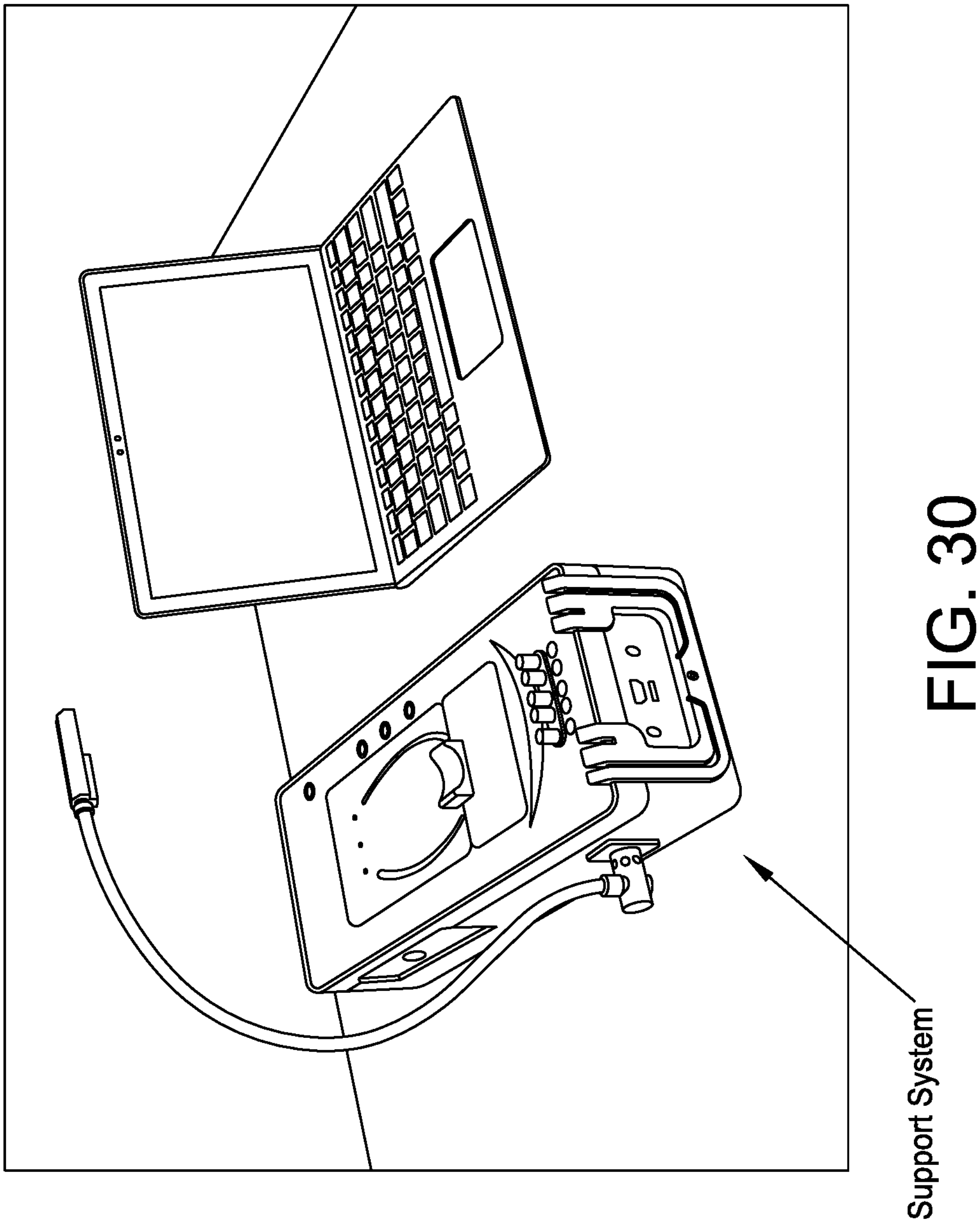
FIGS. 30 and 31 show use of a pair of combined stimulator and bipolar/monopolar electrode assemblies ("light guide electrodes") with a support system.
Figure 31:
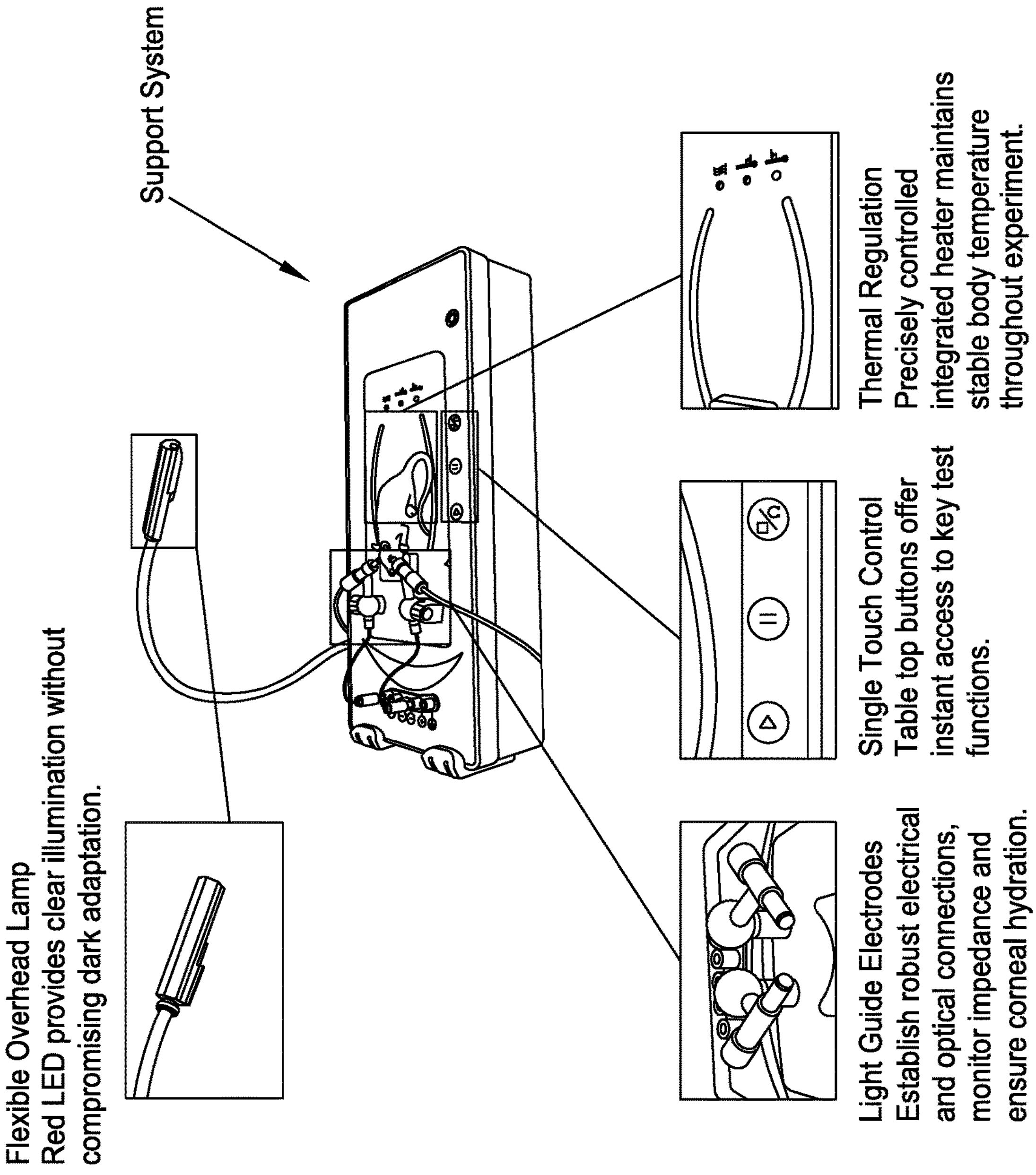
Figure 32:
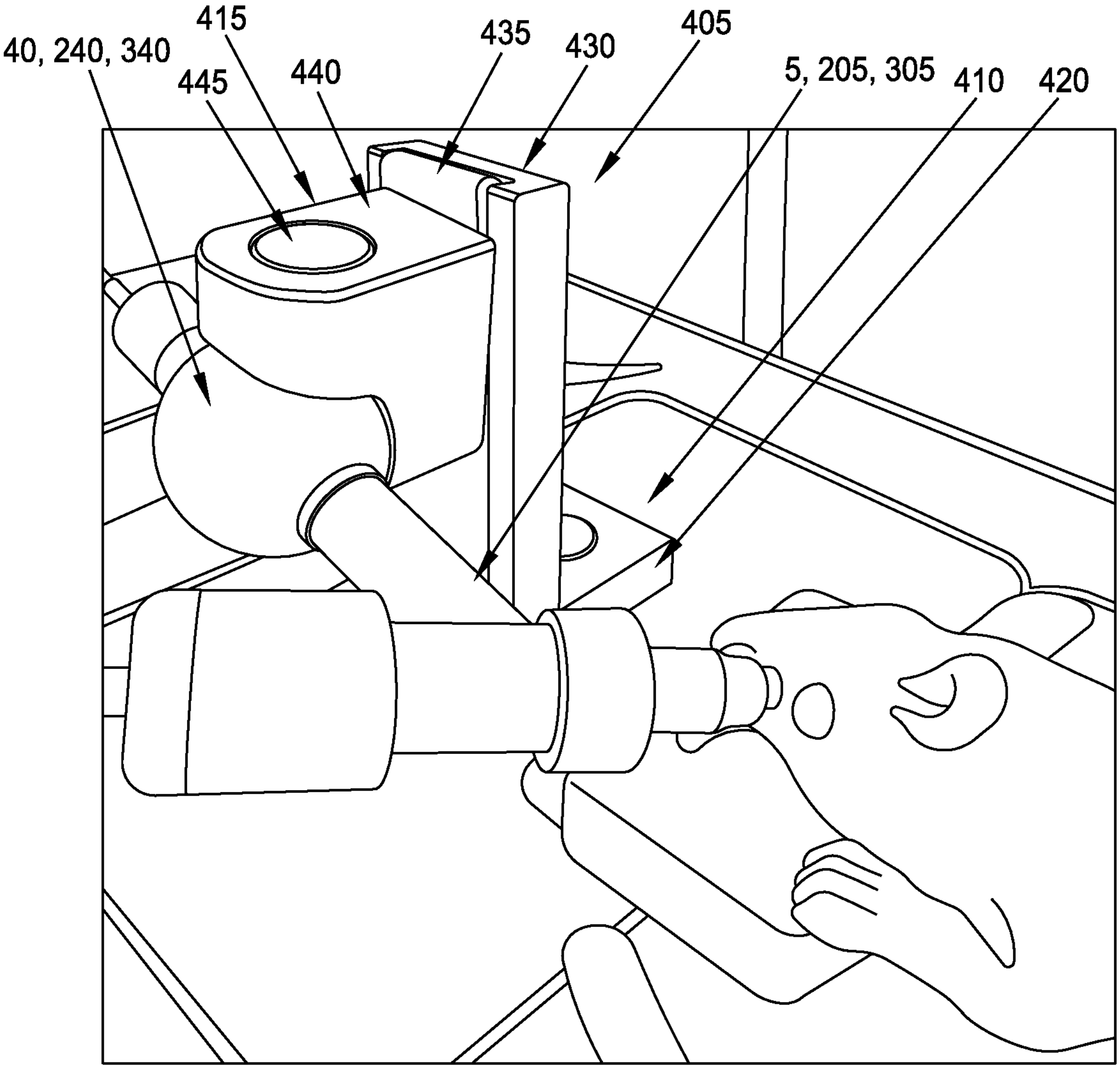
FIGS. 32-42 are schematic views showing an adjustable mount seat for receiving and supporting the magnetic mount of a combined stimulator and bipolar/monopolar electrode assembly.
Figure 33:
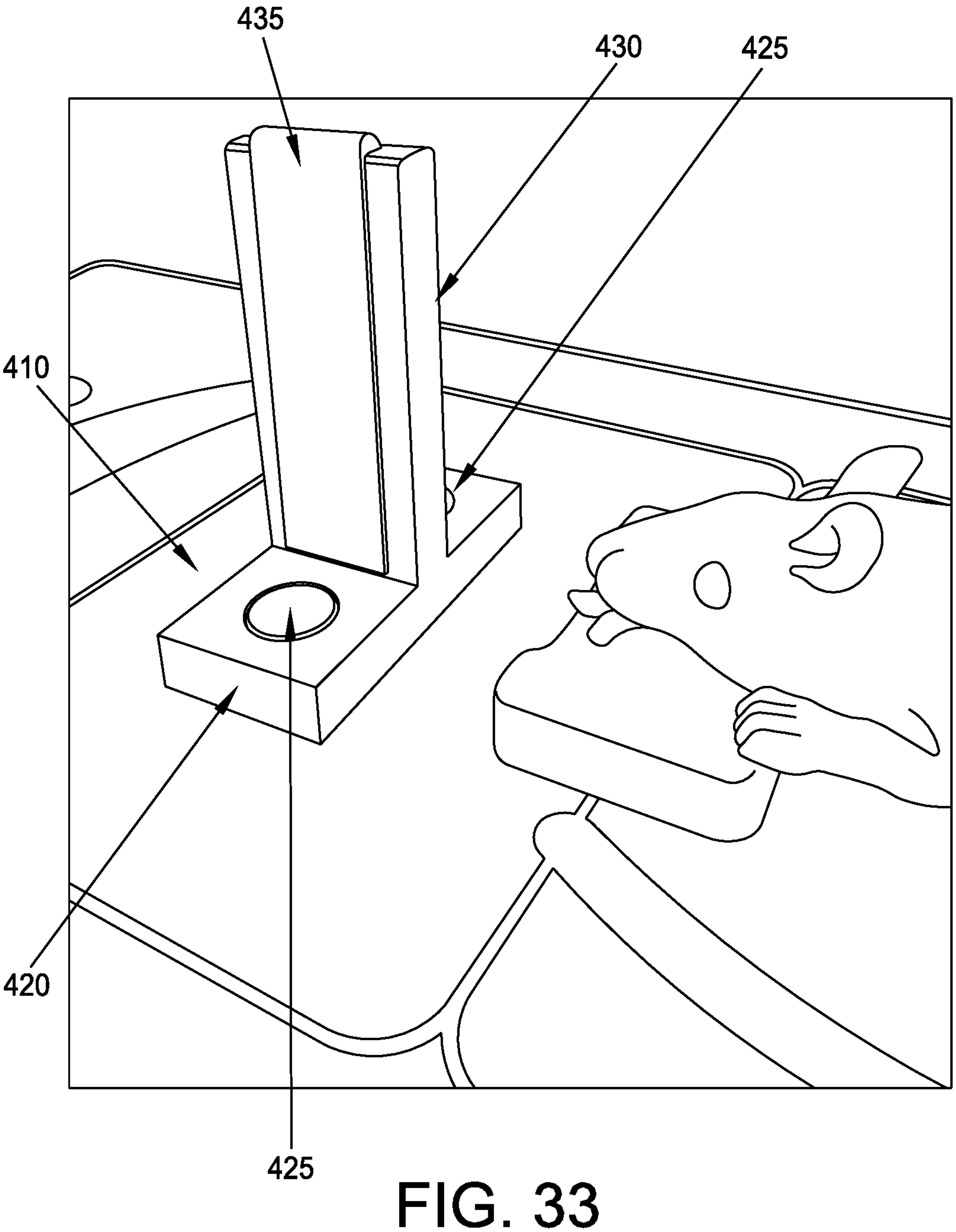
Figure 34:
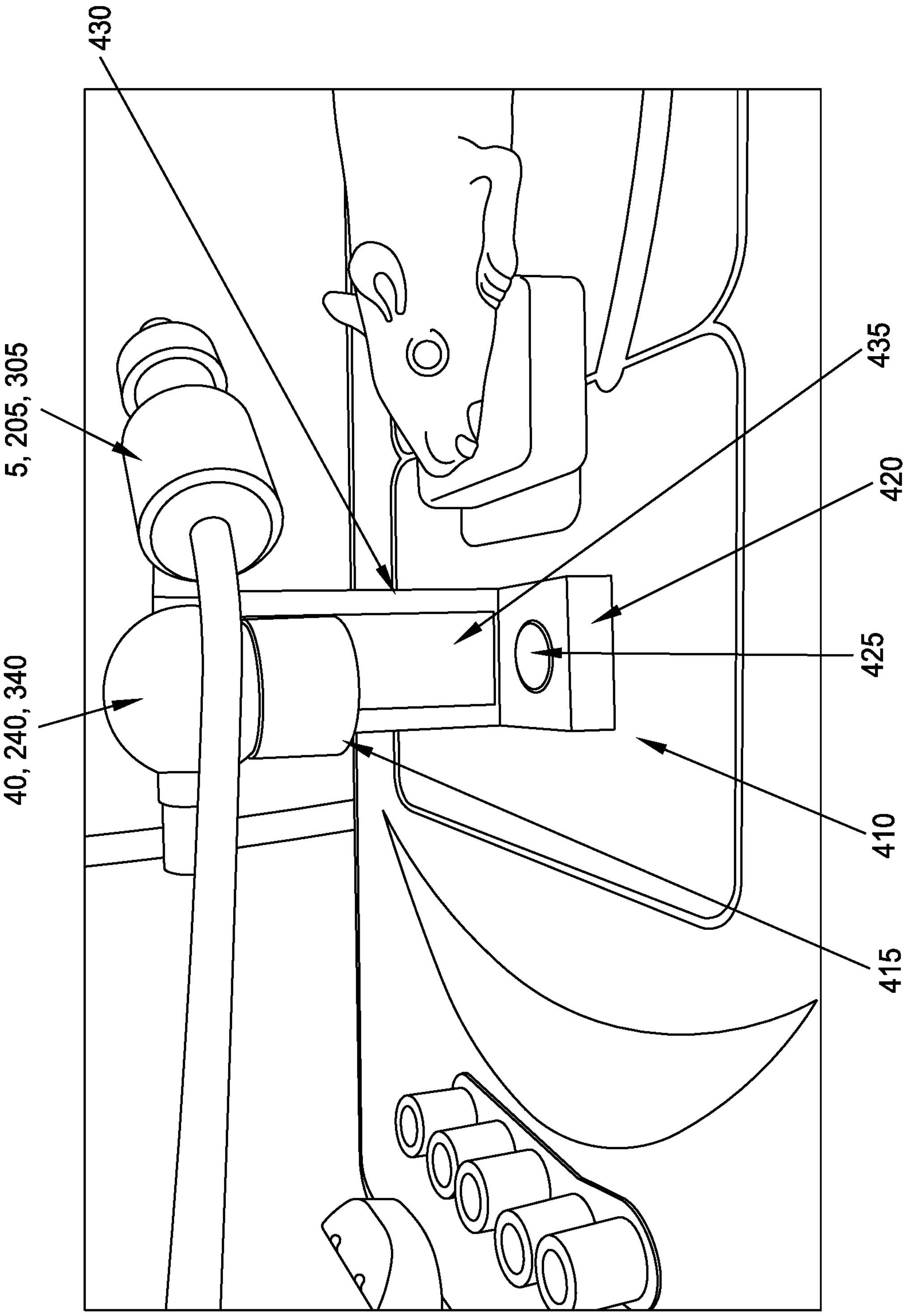
Figure 35:
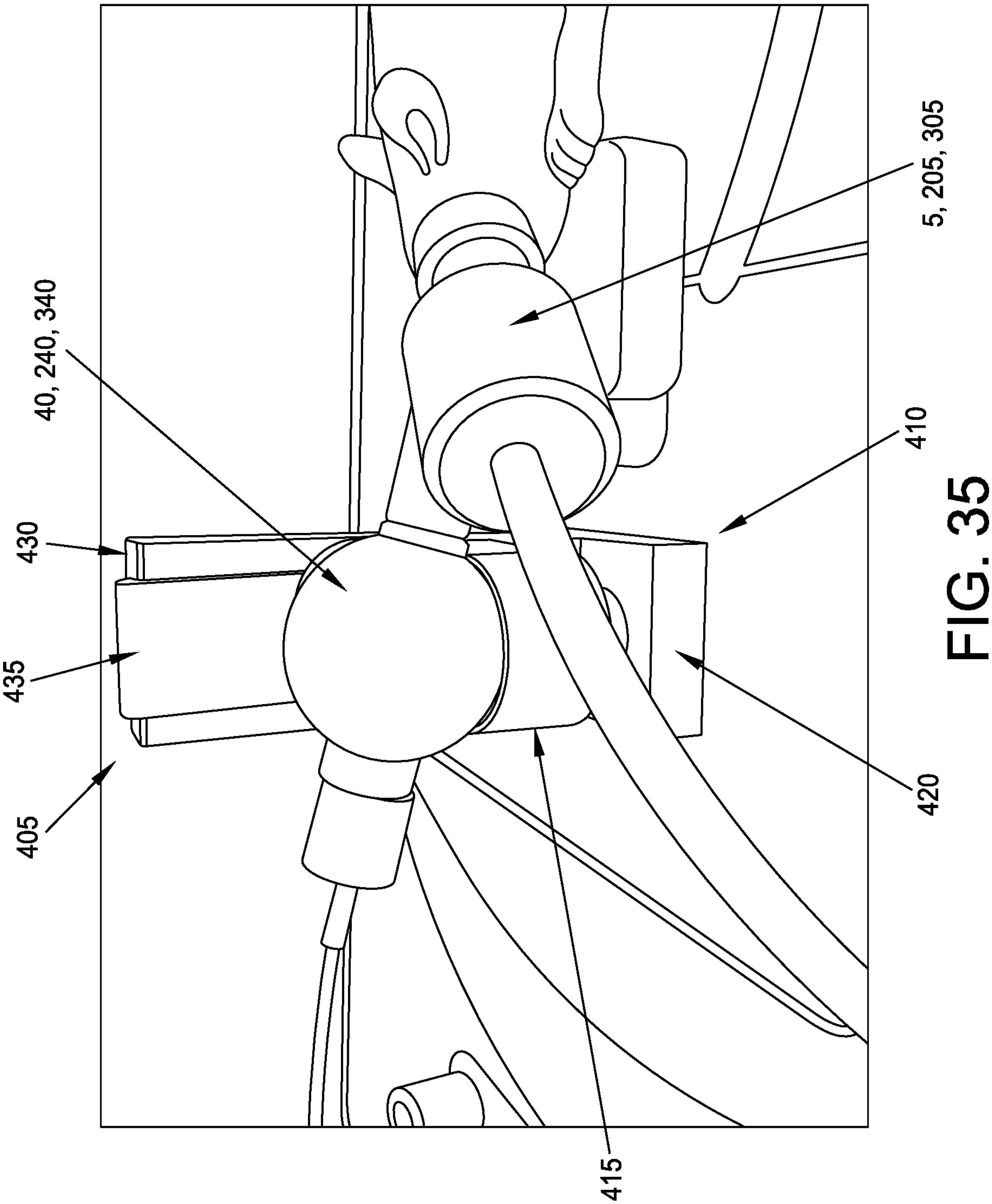
Figure 36:
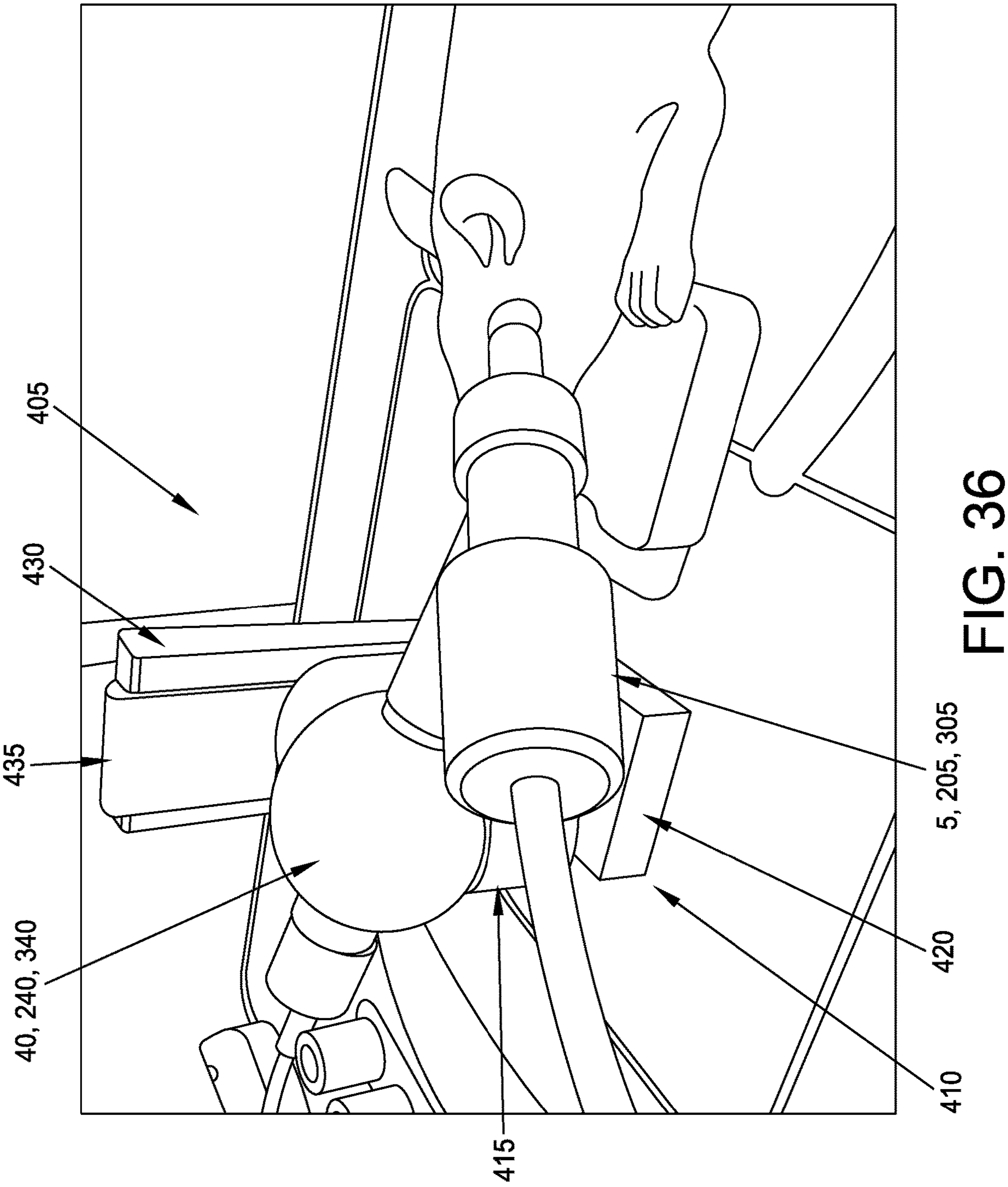
Figure 38:
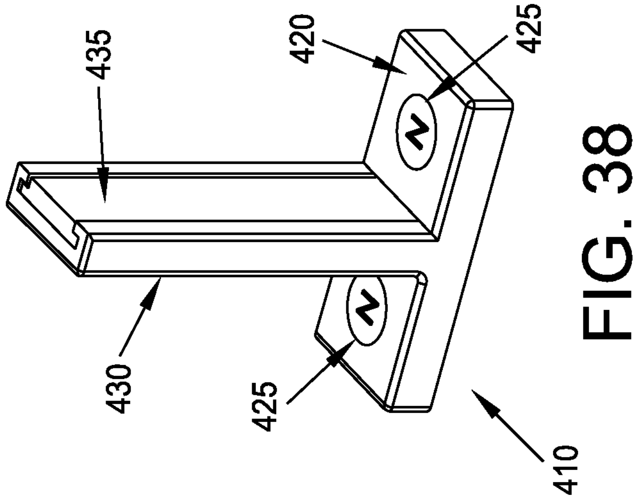
Figure 37:
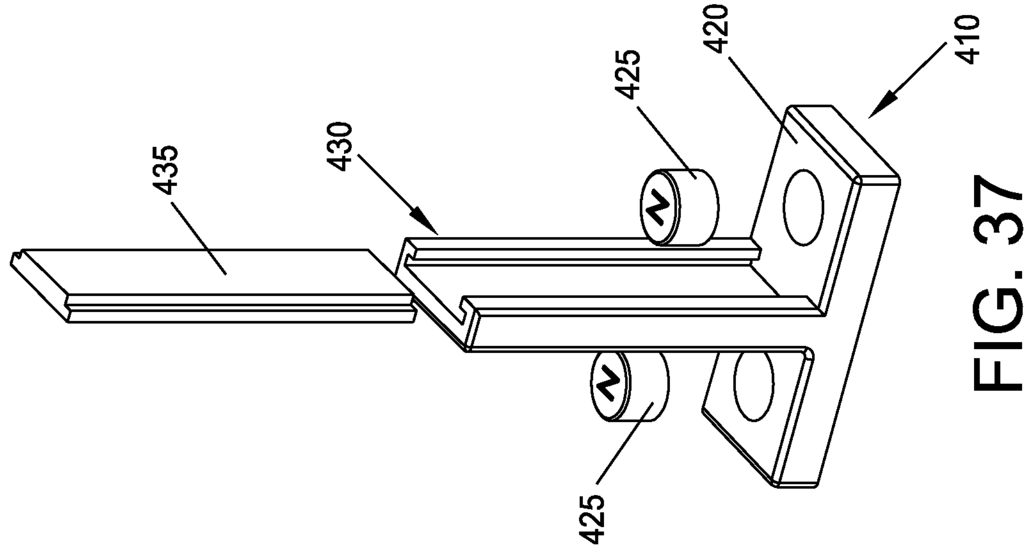
Figure 39:
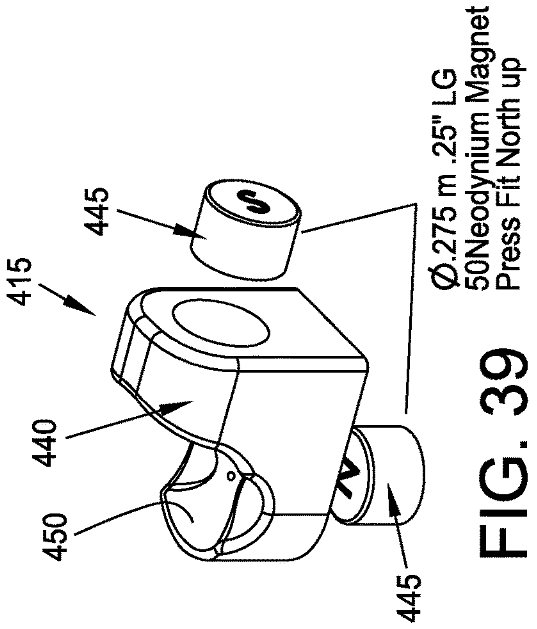
Figure 40:
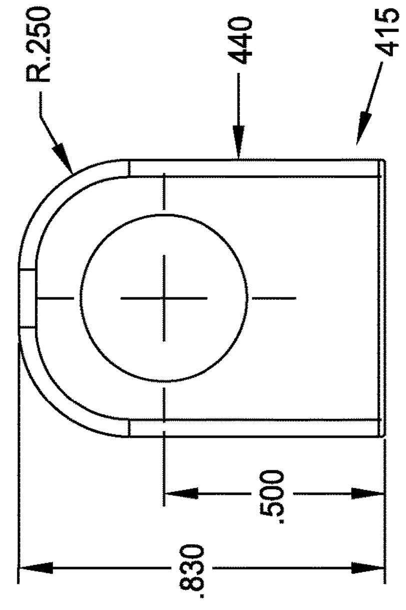
Figure 41:
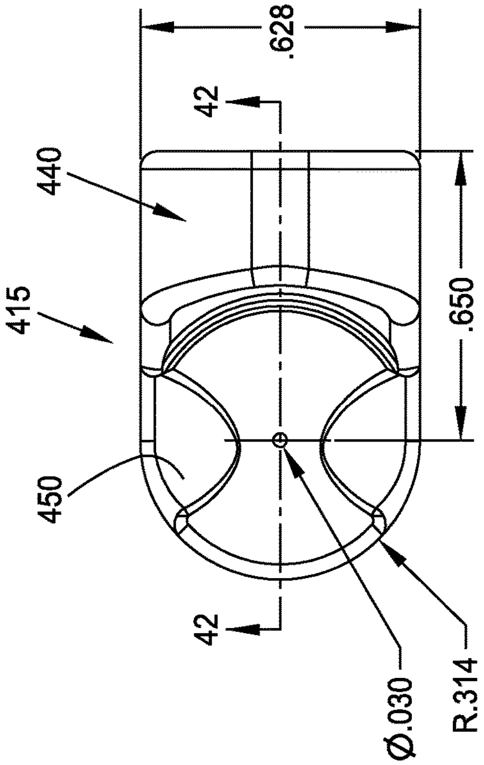
Figure 42:
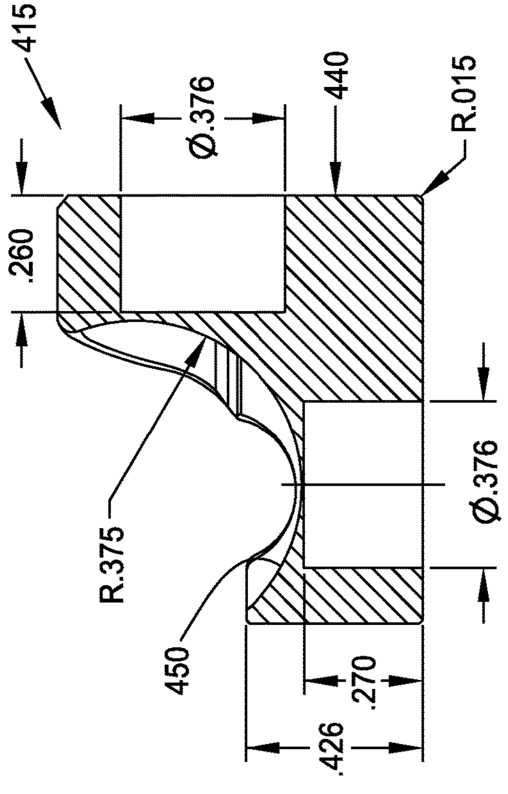

Support System for a Pair of the Combined Stimulator and Bipolar/Monopolar Electrode Assemblies A pair of the combined stimulator and bipolar/monopolar electrode assemblies (e.g., the aforementioned combined stimulator and bipolar electrode assembly 5, and/or the aforementioned combined stimulator and monopolar electrode assembly 5, and/or the aforementioned combined pattern stimulator and monopolar electrode assembly 205, and/or the aforementioned combined pattern stimulator and monopolar electrode assembly 305) is preferably utilized in conjunction with a support system. In one preferred form of the invention, and looking now at FIGS. 30 and 31, the support system comprises a small box that incorporates a heated bed for the mice, an illuminating red light to provide illumination while preserving dark adaptation when setting up the animals, a two-channel, 32-bit amplifier system with indicator lights adjacent each input to indicate any connection problems, all-magnetic fasteners situated on a one-piece, waterproof Lexan bed for easy cleaning, connections for driving all stimulators, provision for a magnetically-attached mask for gas anesthesia and a USB port to communicate with a driving computer.

In one preferred form of the invention, and looking now at FIGS. 32-42, a novel adjustable mount seat 405 receives and supports the magnetic mounts of the combined stimulator and bipolar/monopolar electrode assemblies (e.g., the aforementioned magnetic mount 40 of combined stimulator and bipolar electrode assembly 5, and/or the aforementioned magnetic mount 40 of combined stimulator and monopolar electrode assembly 5, and/or the aforementioned magnetic mount 240 of combined pattern stimulator and monopolar electrode assembly 205, and/or the aforementioned magnetic mount 340 of combined pattern stimulator and monopolar electrode assembly 305).

More particularly, adjustable mount seat 405 generally comprises a vertical support 410 and a ball seat 415. Vertical support 410 comprises a base 420 carrying a pair of magnets 425 and a vertical riser 430 carrying a metallic face 435. Ball seat 415 comprises a body 440 carrying a pair of magnets 445 and defining a spherical recess 450. Magnets 425 of vertical support 410 adjustably mount vertical support 410 to the aforementioned box of the support system. Magnets 445 of ball seat 415 adjustably mount ball seat 415 to metallic face 435 of vertical riser 430. Spherical recess 450 of ball seat 415 receives and supports the magnetic mounts of the combined stimulator and bipolar/monopolar electrode assemblies (e.g., the aforementioned magnetic mount 40 of combined stimulator and bipolar electrode assembly 5, and/or the aforementioned magnetic mount 40 of combined stimulator and monopolar electrode assembly 5, and/or the aforementioned magnetic mount 240 of combined pattern stimulator and monopolar electrode assembly 205, and/or the aforementioned magnetic mount 340 of combined pattern stimulator and monopolar electrode assembly 305).

On account of the foregoing construction, a combined stimulator and bipolar/monopolar electrode assembly can be adjustably mounted to the aforementioned box of the support system by (i) adjustably mounting a magnetic mount 40 (or 240 or 340) in spherical recess 450 of ball seat 415, (ii) adjustably mounting ball seat 415 to vertical support 410, and (iii) adjustably mounting base 420 of vertical support 410 to the aforementioned box of the support system.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for evoking and sensing ophthalmic physiological signals in an eye, the apparatus comprising:

a light source for generating a pattern of light;

an elongated light pipe having a longitudinal axis, a distal end and a proximal end, wherein the proximal end of the elongated light pipe is configured to receive the pattern of light generated by the light source and transmit the pattern of light to the distal end of the elongated light pipe, and further wherein the distal end of the elongated light pipe terminates in a spheroidal recess comprising a pinhole aperture; and an electrode having a distal end and a proximal end, the electrode being mounted to the elongated light pipe and extending proximally along the elongated light pipe so that the distal end of the electrode terminates adjacent to the spheroidal recess at the distal end of the elongated light pipe;

wherein the pinhole aperture is configured to focus the pattern of light generated by the light source so as to evoke ophthalmic physiological signals in the eye disposed in the spheroidal recess of the elongated light pipe.

2. Apparatus according to claim 1 wherein the elongated light pipe comprises a configuration selected from the group consisting of cylindrical, non-linear pseudo-cylindrical, and tapered.

3. Apparatus according to claim 2 wherein the tapered configuration of the elongated light pipe comprises one from the group consisting of conical and frustoconical.

4. Apparatus according to claim 1 wherein the spheroidal recess is sized to match the curvature of the eye of a mouse.

5. Apparatus according to claim 1 wherein the pinhole aperture is formed on the surface of the spheroidal recess.

6. Apparatus according to claim 1 wherein the elongated light pipe comprises a light-transmissive material having a small acceptance angle.

7. Apparatus according to claim 6 wherein the elongated light pipe comprises acrylic glass, polycarbonate, or glass.

8. Apparatus according to claim 1 wherein the elongated light pipe comprises an air-filled spacer.

9. Apparatus according to claim 1 wherein the distal end of the electrode comprises an arcuate configuration disposed adjacent to the spheroidal recess at the distal end of the elongated light pipe.

10. Apparatus according to claim 9 wherein the arcuate configuration comprises a ring.

11. Apparatus according to claim 1 wherein the light source comprises light-emitting diodes (LEDs).

12. Apparatus according to claim 11 wherein the LEDs comprise at least one red LED, at least one green LED and at least one blue LED, and/or at least one ultraviolet LED.

13. Apparatus according to claim 11 wherein the LEDs comprise organic light-emitting diodes (OLEDs) of the sort which do not produce a flash artifact.

14. Apparatus according to claim 1 wherein the light source further comprises appropriate optics for transmitting the light pattern generated by the light source into the light pipe.

15. Apparatus according to claim 1 wherein the pattern of light comprises at least one from the group consisting of alternating light and dark horizontal bars, gratings and checkerboard patterns.

16. Apparatus according to claim 1 further comprising an adjustable mount for supporting the elongated light pipe.

17. Apparatus according to claim 16 wherein the adjustable mount comprises a magnetic ball mount.

18. Apparatus according to claim 1 further comprising a second electrode having a distal end and a proximal end, the second electrode being mounted to the elongated light pipe and extending proximally along the elongated light pipe so that the distal end of the second electrode terminates at the spheroidal recess at the distal end of the elongated light pipe;

wherein the distal end of the electrode is located closer to the longitudinal axis of the elongated light pipe than the distal end of the second electrode.

19. Apparatus according to claim 1 further comprising additional apparatus for evoking and sensing ophthalmic physiological signals in a second eye, the additional apparatus comprising:

a second light source for generating a pattern of light;

a second elongated light pipe having a longitudinal axis, a distal end and a proximal end, wherein the proximal end of the second elongated light pipe is configured to receive the pattern of light generated by the second light source and transmit the pattern of light generated by the second light source to the distal end of the second elongated light pipe, and further wherein the distal end of the second elongated light pipe terminates in a spheroidal recess comprising a pinhole aperture; and a second electrode having a distal end and a proximal end, the second electrode being mounted to the second elongated light pipe and extending proximally along the second elongated light pipe so that the distal end of the second electrode terminates at the spheroidal recess at the distal end of the second elongated light pipe.

20. Apparatus according to claim 19 wherein the electrode is connected the active side of a differential amplifier, and the second electrode is connected to the reference side of the same differential amplifier, and further wherein the active and reference sides of the differential amplifier share a common rail.

21. A method for evoking and sensing ophthalmic physiological signals in an eye, the method comprising:

providing apparatus comprising:

a light source for generating a pattern of light;

an elongated light pipe having a longitudinal axis, a distal end and a proximal end, wherein the proximal end of the elongated light pipe is configured to receive the pattern of light generated by the light source and transmit the pattern of light to the distal end of the elongated light pipe, and further wherein the distal end of the elongated light pipe terminates in a spheroidal recess comprising a pinhole aperture; and a first electrode having a distal end and a proximal end, the first electrode being mounted to the elongated light pipe and extending proximally along the elongated light pipe so that the distal end of the electrode terminates at the spheroidal recess at the distal end of the elongated light pipe;

wherein the pinhole aperture is configured to focus the pattern of light generated by the light source so as to evoke ophthalmic physiological signals in a first eye disposed in the spheroidal recess of the elongated light pipe;

positioning the spheroidal recess of the elongated light pipe against the first eye of a test subject; and introducing the pattern of light into the proximal end of the elongated light pipe.

22. A method according to claim 21 wherein the pattern of light comprises at least one from the group consisting of alternating light and dark horizontal bars, gratings and checkerboard patterns.

23. A method according to claim 22 wherein the pattern of light is produced by light-emitting diodes (LEDs), and further wherein the LEDs comprise organic light-emitting diodes (OLEDs) of the sort which do not produce a flash artifact.

24. A method according to claim 21 further comprising:

providing additional apparatus for evoking and sensing ophthalmic physiological signals in a second eye, the additional apparatus comprising:

a second light source for generating a pattern of light;

a second elongated light pipe having a longitudinal axis, a distal end and a proximal end, wherein the proximal end of the second elongated light pipe is configured to receive the pattern of light generated by the second light source and transmit the pattern of light generated by the second light source to the distal end of the second elongated light pipe, and further wherein the distal end of the second elongated light pipe terminates in a spheroidal recess comprising a pinhole aperture; and a second electrode having a distal end and a proximal end, the second electrode being mounted to the second elongated light pipe and extending proximally along the second elongated light pipe so that the distal end of the second electrode terminates at the spheroidal recess at the distal end of the second elongated light pipe;

positioning the spheroidal recess of the second elongated light pipe against the second eye of a test subject;

introducing the pattern of light into the proximal end of the second elongated light pipe; and determining the electrophysiological response of the first eye by reading electrical signals on the first electrode and determining the electrophysiological response of the second eye by reading electrical signals on the second electrode.

25. A method according to claim 24 wherein electrical signals on the first electrode and the second electrode are read by connecting the first electrode to the active side of a differential amplifier, and the second electrode to the reference side of the same differential amplifier, and further wherein the active and reference sides of the differential amplifier share a common rail.

* * * * *